United States Patent [19]

Hiraoka et al.

[11] 3,960,845

[45] June 1, 1976

[54] PROCESS FOR PREPARING 7β-ACYLAMINO-7α-ALKOXYCEPHALOSPORINS OR 6β-ACYLAMINO-6α-ALKOXYPENICILLINS

[75] Inventors: Tetsuo Hiraoka; Yukio Sugimura, both of Tokyo, Japan

[73] Assignee: Sankyo Company Limited, Tokyo, Japan

[22] Filed: Mar. 4, 1975

[21] Appl. No.: 555,195

[30] Foreign Application Priority Data

| Mar. 22, 1974 | Japan | 49-32391 |
| Mar. 22, 1974 | Japan | 49-32392 |
| Apr. 8, 1974 | Japan | 49-39730 |
| Apr. 13, 1974 | Japan | 49-41530 |

[52] U.S. Cl............. 260/239.1; 260/243 C; 424/246; 424/271
[51] Int. Cl.²............ C07D 499/44; C07D 501/20
[58] Field of Search........ 260/239.1, 243 C, 243 CS

[56] References Cited
UNITED STATES PATENTS

| 3,778,432 | 12/1973 | Pines | 260/239.1 |
| 3,843,641 | 10/1974 | Christensen et al. | 260/239.1 |

OTHER PUBLICATIONS
Firestone et al, J. Org. Chem. 38 1436 (1973).
Koppel et al., J. Amer. Chem. Soc. 95 2403 (1973).

*Primary Examiner*—Gerald A. Schwartz
*Attorney, Agent, or Firm*—Flynn & Frishauf

[57] ABSTRACT

A process for preparing a 7β-acylamino-7αalkoxycephalosporin or 6β-acylamino-6α-alkoxypenicillin which comprises either (a) reacting a 7β-(α'-halogeno or α'-hydroxyacylamino)cephalosporin or 6β-(α'halogeno or α'-hydroxyacylamino)penicillin with a halogenating agent to give a α-halogeno-iminohalide, reacting the latter compound with an equimolar amount of an alkali metal alkoxide in the presence of one equivalent amount of a base to give a 7α-alkoxyketeneimine and subjecting the latter compound to hydration; or (b) reacting the 7β-(α'-halogeno or α'hydroxyacylamino)cephalosporin or 6β-(α'-halogeno or α'-hydroxyacylamino) penicillin with the halogenating agent to give the α-halogeno-iminohalide, reacting the latter compound with two equimolar amounts of the alkali metal alkoxide in the presence of one equivalent amount of the base to give a dialkoxyimino compound, reacting the latter compound with a halogeno-silyl compound or an acid and treating the resulting product with water.

The final products are useful as antibacterial agents or intermediates thereof.

27 Claims, No Drawings

PROCESS FOR PREPARING 7β-ACYLAMINO-7α-ALKOXYCEPHALOSPORINS OR 6β-ACYLAMINO-6α-ALKOXYPENICILLINS

This invention relates to a novel process for preparing a compound having the formula

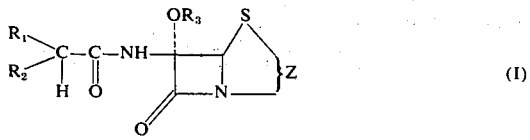
(I)

wherein $R_1$ represents hydrogen atom, a halogen atom, cyano group, an alkoxycarbonyl group, an acylamino group, an alkoxycarbonylamino group, an optionally substituted - alkyl group, - alkenyl group, - alkynyl group, - aryl group, - aralkyl group, - alkylthio group, - alkenylthio group, - alkynylthio group, - arylthio group, - aralkylthio group, - carbamoyl group, - alkylsulfonyl group or - aminosulfonyl group; $R_2$ represents hydrogen atom, a halogen atom, cyano group, an alkoxycarbonyl group, an optionally substituted - alkyl group, - alkenyl group, - alkynyl group, - aryl group, - aralkyl group, - alkylthio group, alkenylthio group, - alkynylthio group, - arylthio group, - aralkylthio group, - alkyloxy group, - alkenyloxy group, - alkynyloxy group, - aryloxy group, - aralkyloxy group, - heterocyclic group, - heterocyclic oxy group or - heterocyclic thio group; $R_3$ represents a lower alkyl group or an optionally substituted aralkyl group;
Z represents a fragment of the formula

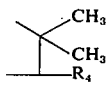

or

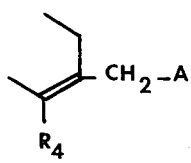

wherein $R_4$ represents carboxyl group or a protected carboxyl group,
A represents hydrogen, azido or the formula -B-E in which B is oxygen or sulfur and E is acyl, lower alkyl, optionally substituted-carbamoyl, -thiocarbamoyl or -heterocyclic group.

In the above formula (I), $R_1$ is preferably hydrogen atom, a halogen atom, e.g., chlorine, bromine or iodine, an alkyl group having 1 – 4 carbon atoms, e.g., methyl, ethyl, n-propyl, isopropyl or n-butyl, or an aryl group, e.g., phenyl or naphthyl; $R_2$ is preferably hydrogen atom, a halogen atom, e.g., chlorine, bromine or iodine, an alkyl group having 1 – 4 carbon atoms, e.g., methyl, ethyl, n-propyl, isopropyl, n-butyl, isobutyl or tert-butyl, an aryl group, e.g., phenyl or naphthyl, an alkylthio group having 1 – 4 carbon atoms, e.g., methylthio, ethylthio, n-propylthio or isopropylthio, an alkynylthio group having 2 – 4 carbon atoms, e.g., propargylthio, an arylthio group, e.g., phenylthio, an azidoalkylthio group having 1 – 4 carbon atoms, e.g., azidomethylthio or azidoethylthio, a cyanoalkylthio group having 1 – 4 carbon atoms in the alkyl moiety, e.g., cyanomethylthio or cyanoethylthio, an alkylsulfonyl group having 1 – 4 carbon atoms, e.g., methyl sulfonyl or ethylsulfonyl a 5- or 6-membered heterocyclic thio group containing one or more of sulfur, nitrogen and/or oxygen atoms in the ring which may be substituted with a lower alkyl group having 1 – 3 carbon atoms, e.g., imidazolylthio, thiadiazolylthio, triazolylthio, thienylthio, isoxazolylthio, methylisoxazolylthio, tetrazolylthio, methyltetrazolylthio, pyrimidinylthio or pyridylthio, a 5- or 6-membered heterocyclic oxy group containing one or more of sulfur, nitrogen and/or oxygen atom in the ring which may be substituted with a lower alkyl group having 1 – 3 carbon atoms, e.g., isoxazolyloxy, methylisoxazolyloxy, imidazolyloxy, thiadiazolyloxy, triazolyloxy, thienyloxy, tetrazolyloxy, methyltetrazolyloxy, pyrimidinyloxy, or pyridyloxy, a 5- or 6-membered heterocyclic group containing one or more of sulfur, nitrogen and/or oxygen atom in the ring which may be substituted with a lower alkyl group having 1 – 3 carbon atoms, e.g., thienyl, imidazolyl, thiadiazolyl, isoxazolyl, methylisoxazolyl, tetrazolyl, methyltetrazolyl, pyrimidinyl or a pyridyl, and alkylsulfonyl group having 1 – 4 carbon atoms, e.g., methylsulfonyl, ethylsulfonyl or n-propylfulfonyl; $R_3$ is preferably an alkyl group having 1 – 4 carbon atoms, e.g., methyl, ethyl, n-propyl, isopropyl or n-butyl; $R_4$ is carboxyl group or a protected carboxyl group such as an alkoxycarbonyl group having 1 – 4 carbon atoms in the alkyl moiety, e.g., methoxycarbonyl, ethoxycarbonyl, n-propoxycarbonyl or n-butoxycarbonyl, a halogenoalkoxycarbonyl group having 1 – 4 carbon atoms in the alkyl moiety, e.g., dichloroethoxycarbonyl or trichloroethoxycarbonyl, a benzyloxycarbonyl group optionally substituted with halogen, methoxy or nitro, e.g., benzyloxycarbonyl, p-chlorobenzyloxycarbonyl, p-methoxy benzyloxycarbonyl or p-nitrobenzyloxycarbonyl, diphenylmethyloxycarbonyl group, a trialkylsilyloxycarbonyl group having 1 – 4 carbon atoms in each alkyl moiety, e.g., trimethylsilyloxycarbonyl or triethylsilyloxycarbonyl, a dialkylhalogenosilyloxycarbonyl group having 1 – 4 carbon atoms in each alkyl moiety, e.g., dimethylchlorosilyloxycarbonyl or dimethylbromosilyloxycarbonyl, a phenacyloxycarbonyl group optionally substituted with halogen, or methoxy, e.g., p-chlorophenacyloxycarbonyl, p-bromophenacyloxycarbonyl, p-methoxyphenacyloxycarbonyl or an acyloxycarbonyl, e.g., acetoxycarbonyl or benzoyloxycarbonyl, a halogenoacylcarbonyl group, e.g., chloroacetoxycarbonyl or bromoacetoxycarbonyl, a dihalogenophosphinooxycarbonyl group, e.g., dichlorophosphinooxycarbonyl or dibromophosphinooxycarbonyl, a dialkylphosphinoxycarbonyl group, e.g., dimethylphosphinoxycarbonyl or an aminocarbonyl group, e.g., 3-oxo-2,3-dihydro-s-triazolo[4,3-a]pyridone-3-ylcarbonyl or saccharylcarbonyl; E is preferably an acyl group, e.g., acetyl, propionyl or benzoyl, carbamoyl group or a 5- or 6-membered heterocyclic group, which may be substituted with a lower alkyl group having 1 – 3 carbon atoms, e.g., tetrazolyl, 1-methyltetrazolyl, isoxazolyl, imidazolyl, thiazolyl, triazolyl, thienyl, thiadiazolyl, methylthiadiazolyl, pyrimidinyl or pyridyl.

Heretofore, there have been known various processes for introducing an alkoxy group into 7-position of cephem ring or 6-position of penam ring, of which the alkoxylation with t-butylhypochlorite and lithium alkoxide is the simplest to perform and gives the best yield [R. A. Firestone and B. G. Christensen, J. Org. Chem. 38, 1436 (1973); G. A. Koppel and R. E. Koehler, J. Amer. Chem. Soc. 95, 2403 (1973)]. However, this method has the disadvantage that it is not applicable in the case of cephalosporins or penicillins which are sensitive to t-butylhypochlorite, namely, have an anion formation center in the side chain.

It is thus an object of the present invention to provide a novel and generally applicable process for preparing the 7β-acylamino-7α-alkoxycephalosporin or 6β-acylamino-6α-alkoxypenicillin having the formula (I) which are valuable as antibacterial agents or intermediates thereof.

In accordance with the present invention, the compound having the formula (I) can be prepared by either (a) reacting an acylamino compound having the formula

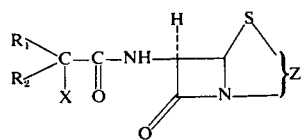
(II)

wherein $R_1, R_2$ and Z are the same as above and X represents hydroxy group or a halogen atom with a halogenating agent to give a halogenoimine having the formula

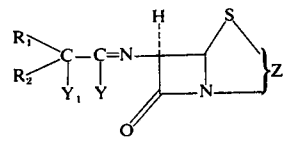
(III)

wherein $R_1, R_2$ and Z are the same as above and $Y_1$ and Y may be the same or different and each represents a halogen atom, reacting the latter compound (III) with an equimolar amount of an alkali metal alkoxide having the formula $R_3OM$ (IV)

wherein $R_3$ is the same as above and M represents an alkali metal in the presence of one equivalent amount of a base to give an alkoxyketeneimine having the formula

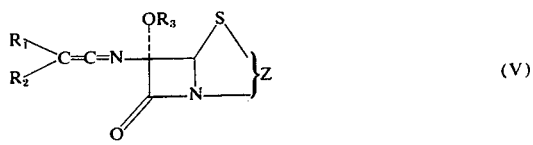
(V)

wherein $R_1, R_2, R_3$ and Z are the same as above and subjecting the latter compound (V) to hydration, or (b) reacting the above acylamino compound (II) with a halogenating agent to give the above halogenoimine (III), reacting the latter compound (III) with two equimolar amounts of the above alkali metal alkoxide in the presence of one equivalent amount of a base to give a dialkoxyimino compound having the formula

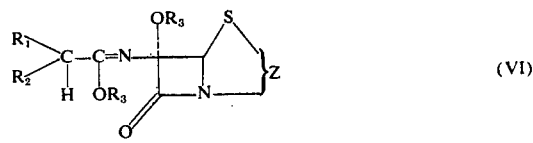
(VI)

wherein $R_1, R_2, R_3$ and Z are the same as above, reacting the latter compound (VI) with a halogenosilyl compound or an acid and treating the resulting compound with water.

The reactions in the present process may be illustrated by the following reaction sequence.

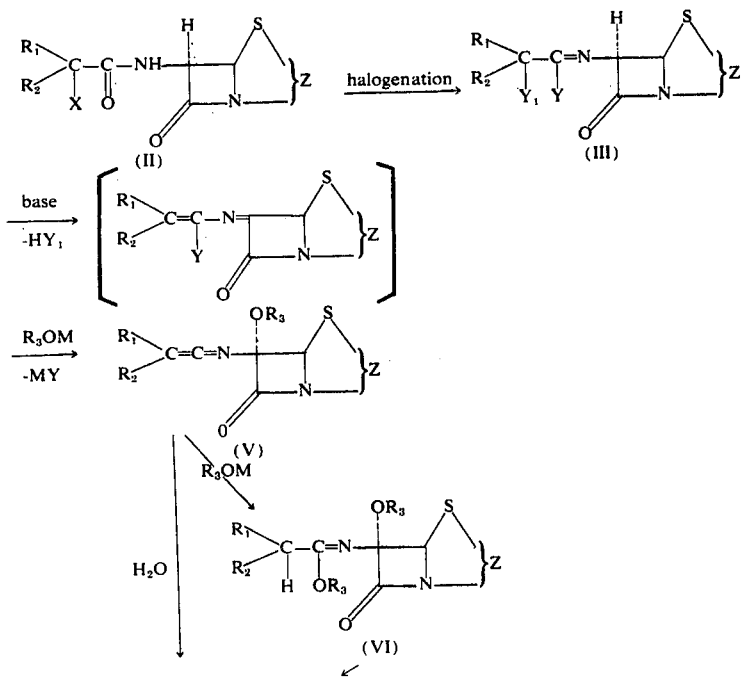

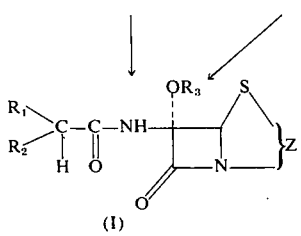

(I)

In the above formula, $R_1$, $R_2$, $R_3$, X, Y, $Y_1$, Z and M are the same as above.

According to the present invention, the compound (III) is prepared by reacting the compound (II) with a halogenating agent. In the above reaction, the halogenating agent includes a phosphorus pentahalide, e.g., phosphorus pentachloride, - bromide; a phosphorus trihalide, e.g., phosphorus trichloride, - bromide; a phosphorus oxyhalide, e.g., phosphorus oxychloride, - bromide; and a thionyl halide, e.g., thionyl chloride, - bromide. Phosphorus pentachloride can be most preferably employed.

The reaction is carried out in an anhydrous inert organic solvent under stirring at temperatures of from −50°C. to 40°C. for 15 minutes − 5 hours. Suitable reaction media are inert organic solvent such as chloroform, methylene chloride, benzene, ether, tetrahydrofuran and dioxane. The reaction may be preferably conducted in the presence of a tertiary amine such as quinoline, diethylaniline, dimethylaniline, pyridine, triethylamine and diazabicyclooctane.

After completion of the reaction, the reaction mixture including the compound (III) as such can be employed as a starting material in the next step. But the reaction product, if desired, can be recovered and purified by conventional means.

In the above reaction, the group $R_4$ in the formula (II) must be a protected carboxyl group and, in case where X is hydroxy group, it is substituted by a halogen atom.

The compound (V) is prepared by reacting the compound (III) with an equimolar amount of the alkali metal alkoxide (IV) in the presence of one equivalent amount of a base. In the reaction, the alkali metal alkoxide (IV) includes lithium methoxide, - ethoxide, sodium methoxide, - ethoxide, potassium methoxide and - ethoxide. The base includes an inorganic base such as alkali metal hydroxides, e.g., sodium hydroxide or potassium hydroxide, alkali metal carbonates, e.g., sodium carbonate or potassium carbonate, alkali metal hydrides, e.g., sodium hydride or potassium hydride, alkali metal alkoxide, e.g., lithium methoxide, sodium methoxide or potassium methoxide and a tertiary amine such as trialkylamines, e.g., trimethylamine or triethylamine, dialkylanilines, e.g., dimethylaniline, diethylaniline or pyridine, quinoline and pyridine. Most preferably, there can be employed the alkali metal alkoxide (IV) as the base. The reaction is preferably carried out in an inert organic solvent at temperatures of from −78°C. to 20°C. for 1 − 60 minutes. Suitable reaction media are inert organic solvents such as chloroform, ether, tetrahydrofuran, dioxane, benzene and alcohol having the formula $R_3OH$ wherein $R_3$ is the same as above. After completion of the reaction, the reaction mixture including the compound (V) as such can be employed as a starting material in the next step. But the reaction product, if desired, can be recovered and purified by conventional means. For instance, the reaction mixture is poured into ice water, extracted with an appropriate organic solvent, washed with water, dried, evaporated to dryness. The residue thus obtained is purified by recrystallization or chromatography.

The compound (I) is prepared by contacting the compound (V) with a diluted mineral acid, or an organic acid, or a diluted organic acid.

The mineral acid includes hydrochloric acid, hydrobromic acid, sulfuric acid, phosphoric acid and perchromic acid. The organic acid includes trifluoroacetic acid, trichloroacetic acid, dichloroacetic acid. The reaction may be preferably carried out in an aqueous organic solvent at temperatures of from −20°C. to 40°C. for 0.5 − 12 hours under stirring.

After completion of the reaction, the desired product (I) can be recovered by conventional means. For instance, the reaction mixture is evaporated to dryness under reduced pressure and to the residue is added ice water. The mixture is extracted with an appropriate organic solvent. The extract is washed with water, dried and evaporated to dryness. The residue is purified by recrystallization or chromatography.

The compound (VI) is prepared by reacting the compound (III) with two equivalents moles of the alkoxides (IV) in the presence of one equivalent mole of a base in an inert organic solvent. There may be employed in this reaction such an alkoxide, a base and a solvent as employed in the preparation of the compound (V). The reaction procedure is also the same as in the preparation of the compound (V).

After completion of the reaction, the reaction mixture as such can be used as a starting material in the next step. The product, if desired, may be recovered and purified by conventional means.

The compound (I) can be also prepared by reacting the compound (VI) with a halogenosilyl compound or an acid and treating the resulting product with water.

The halogenosilyl compound employed in this reaction includes a trialkylhalogenosilane such as trimethylchlorosilane, trimethylbromosilane, triethylchlorosilane or triethylbromosilane and a dialkyldihalogenosilane such as dimethyldichlorosilane, dimethyldibromosilane, diethyldichlorosilane or diethyldibromosilane. The acid includes a mineral acid such as hydrochloric acid, hydrobromic acid, sulfuric acid, phosphoric acid, perchloric acid and a Lewis acid such as boron trifluoride, boron trichloride, aluminum trichloride, tin (IV) chloride or titanium (IV) chloride. The reaction can be preferably carried out by dissolving the compound (VI) in an inert organic solvent, e.g., benzene, toluene, dioxane, ether, carbon tetrachloride, chloroform, methylenechloride, adding the halogenosilyl compound or the acid to the solution, stirring the mixture at temperatures of from −50°C to 40°C. for 5 minutes − 24 hours and adding the resulting mixture to a cold buffer solution (pH 4 − 8).

After completion of the reaction, the desired product may be recovered by conventional means. For example, the reaction mixture is extracted with an appropriate organic solvent, washed with water, dried and evaporated to dryness. The residue is purified by recrystallization or chromatography. Some of the acylamino compounds (II) employed as starting materials in this invention are novel and can be prepared according to known methods, for example, described by E. H. Flynn (Edited) in "Cephalosporins and Penicillins", page 83, Academic Press, New York and London (1972). For instance, they can be prepared by reacting the corresponding amino compounds with halides or anhydrides of carboxylic acids of the formula

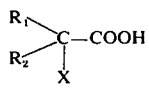

wherein $R_1$, $R_2$ and X are the same as above. The process of this invention has advantages that it is generally applicable to the preparation of cephalosporins and penicillins optionally having an anion formation center in the side chain and that it can be carried out successively without isolation of the intermadiates produced in the reaction system, i.e., in one-pot reaction.

The compounds (I) include novel cephalosporins and penicillins in addition to the known.

As representative novel compounds having the fomula (I) there can be mentioned the following compounds: 7β-chloroacetamido-7α-methoxy-3-methyl-3-cephem-4-carboxylic acid, 7β-chloroacetamido-7α-methoxy-3-carbamoyloxymethyl-3-cephem-4-carboxylic acid, 7β-propionamido-7α-methoxy-3-methyl-3-cephem-4-carboxylic acid, 7β-phenoxyacetamido-7α-methoxy-3-methyl-3-cephem-4-carboxylic acid, 7β-phenylthioacetamido-7α-methoxy-3-acetoxymethyl-3-cephem-4-carboxylic acid, 7β-chloroacetamido-7α-methoxy-3-acetoxymethyl-3-cephem-4-carboxylic acid, 7β-chloroacetamido-7α-methoxy-3-(1-methyl-1H-tetrazol-5-yl)thiomethyl-3-cephem-4-carboxylic acid, 7β-(1,2,4-triazol-4H-3-yl)thioacetamido-7α-methoxy-3-carbamoyloxymethyl-3-cephem-4-carboxylic acid, 7β-(imidazol-2-yl)thioacetamido-7α-methoxy-3-carbamoyloxymethyl-3-cephem-4-carboxylic acid, 7β-(1,3,4-thiadiazol-2-yl)thioacetamido-7α-methoxy-3-carbamoyloxymethyl-3-cephem-4-carboxylic acid, 7β-propargylthioacetamido-7α-methoxy-3-carbamoyloxymethyl-3-cephem-4-carboxylic acid, 7β-cyanomethylthioacetamido-7α-methoxy-3-carbamoyloxymethyl-3-cephem-4-carboxylic acid, 7β-(5-methyl-1,2,4-triazol-4H-3-yl)thioacetamido-7α-methoxy-3-carbamoyloxymethyl-3-cephem-4-carboxylic acid, 7β-(2-pyridyl)thioacetamido-7α-methoxy-3-carbamoyloxymethyl-3-cephem-4-carboxylic acid, 7β-(2-pyrimidyl)thioacetamido-7α-methoxy-3-carbamoyloxymethyl-3-cephem-4-carboxylic acid, 7β-(2-thiozolin-2-yl)thioacetamido-7α-methoxy-3-carbamoyloxymethyl-3-cephem-4-carboxylic acid, 7β-(n-propylthioacetamido)-7α-methoxy-3-carbamoyloxymethyl-3-cephem-4-carboxylic acid, 7β-cyanomethylthioacetamido-7α-methoxy-3-acetoxymethyl-3-cephem-4-carboxylic acid, 7β-(2-imidazolyl)thioacetamido-7α-methoxy-3-acetoxymethyl-3-cephem-4-carboxylic acid, 7β-(1,3,4-thiadiazolyl-2-yl)thioacetamido-7α-methoxy-3-(1-methyl-1H-tetrazol-5-yl)thiomethyl-3-cephem- 4-carboxylic acid, 7β-(2-imidazolyl)thioacetamido-7α-methoxy-3-(1-methyl-1H-tetrazol-5-yl)thiomethyl-3-cephem-4-carboxylic acid, 7β-cyanomethylthioacetamido-7α-methoxy-3-(1-methyl-1H-tetrazol-5-yl)thiomethyl-3-cephem-4-carboxylic acid, 7β-propargylthioacetamido-7α-methoxy-3-(1-methyl-1H-tetrazol-5-yl)thiomethyl-3-cephem-4-carboxylic acid, 7β-bromoacetamido-7α-methoxy-3-carbamoyloxymethyl-3-cephem-4-carboxylic acid, 6β-chloroacetamido-6α-methoxypenicillanic acid, 6β-phenylthioacetamido-6α-methoxypenicillanic acid, 6β-propargylthioacetamido-6α-methoxypenicillanic acid, 6β-(1,3,4-thiadiazol-2-yl)thioacetamido-6α-methoxypenicillanic acid, 7β-chloroacetamido-7α-benzyloxy-3-methyl-3-cephem-4-carboxylic acid and etc. Also, there can be mentioned these cephalosporin or penicillanic acid derivatives in which the carboxyl radical is protected with a methyl, p-methoxybenzyl, bromophenacyl, benzhydryl, trimethylsilyl, 3-oxo-2,3-dihydro-s-triazolo[4,3-a]pyridon-3-yl radical.

Especially, the following compounds have excellent antimicrobial activity against broad pathogenic microorganisms: 7β-(imidazol-2-yl)thioacetamido-7α-methoxy-3-(1-methyl-1H-tetrazol-5-yl)thiomethyl-3-cephem-4-carboxylic acid, 7β-(1,3,4-thiadiazol-2-yl)thioacetamido-7α-methoxy-3-(1-methyl-1H-tetrazol-5-yl)thiomethyl-3-cephem-4-carboxylic acid, 7β-(3-isoxazolyloxy)acetamido-7α-methoxy-3-(1-methyl-1H-tetrazol-5-yl)thiomethyl-3-cephem-4-carboxylic acid, 7β-propargylthioacetamido-7α-methoxy-3-(1-methyl-1H-tetrazol-5-yl)thiomethyl-3-cephem-4-carboxylic acid, 7β-cyanomethylthioacetamido-7α-methoxy-3-(1-methyl-1H-tetrazol-5-yl)thiomethyl-3-cephem-4-carboxylic acid, 7β-(5-methyl-1,3,4-thiadiazol-2-yl)thioacetamido-7α-methoxy-3-(1-methyl-1H-tetrazol-5-yl)thiomethyl-3-cephem-4-carboxylic acid, 7β-(1,2,4-triazol-4H-3-yl)thioacetamido-7α-methoxy-3-carbamoyloxymethyl-3-cephem-4-carboxylic acid, 7β-(imidazol-2-yl)thioacetamido-7α-methoxy-3-carbamoyloxymethyl-3-cephem-4-carboxylic acid, 7β-(1,3,4-thiadiazol-2-yl)thioacetamido-7α-methoxy-3-carbamoyloxymethyl-3-cephem-4-carboxylic acid, 7β-(5-methyl-1,3,4-thiadiazol-2-yl)thioacetamido-7α-methoxy-3-carbamoyloxymethyl-3-cephem-4-carboxylic acid, 7β-propargylthioacetamido-7α-methoxy-3-carbamoyloxymethyl-3-cephem-4-carboxylic acid, 7β-cyanomethylthioacetamido-7α-methoxy-3-carbamoyloxymethyl-3-3-cephem-4-carboxylic acid, 7β-cyanomethylthioacetamido-7α-methoxy-3-acetoxymethyl-3-cephem-4-carboxylic acid, 7β-azidomethylthioacetamido-7α-methoxy-3-acetoxymethyl-3-cephem-4-carboxylic acid, 7β-(1,3,4-thiadiazol-2-yl)thioacetamido-7α-methoxy-3-acetoxymethyl-3-cephem-4-carboxylic acid, 7β-propargylthioacetamido-7α-methoxy-3-acetoxymethyl-3-cephem-4-carboxylic acid, 7β-(imidazol-2-yl)thioacetamido-7α-methoxy-3-acetoxymethyl-3-cephem-4-carboxylic acid, 7β-(3-isoxazolyloxy)acetamido-7α-methoxy-3-acetoxymethyl-3-cephem-4-carboxylic acid, 7β-(3-isoxazolyl)thioacetamido-7α-methoxy-3-acetoxymethyl-3-cephem-4-carboxylic acid, 7β-methylsulfonylacetamido-7α-methoxy-3-(1-methyl-1H-tetrazole-5-yl)thiomethyl-3-cephem-4-carboxylic acid.

The antimicrobial activities of these compounds can be summarized in the following Table:

Table

| Tested compounds | Minimal inhibitory concentrations of various microorganisms mcg/ml | | | | | | | | |
|---|---|---|---|---|---|---|---|---|---|
| | I* | | II | | III | IV | | V | VI |
| | A | B | A | B | | A | B | | |
| 7β-(imidazol-2-yl)thioacetamido-7α-methoxy-3-(1-methyl-1H-tetrazol-5-yl)thiomethyl-3-cephem-4-carboxylic acid | 0.8 | 3.1 | 6.2 | 6.2 | 6.2 | 6.2 | >200 | 12.5 | 3.1 |
| 7β-(1,3,4-thiadiazol-2-yl)thioacetamido-7α-methoxy-3-(1-methyl-1H-tetrazol-5-yl)-thiomethyl-3-cephem-4-carboxylic acid | 0.4 | 0.8 | 1.5 | 1.5 | 1.5 | 1.5 | >200 | 3.1 | 0.8 |
| 7β-(3-isoxazolyloxy)acetamido-7α-methoxy-3-cephem-4-carboxylic acid | 0.2 | 0.8 | 3.1 | 3.1 | 3.1 | 3.1 | >400 | 6.2 | 1.5 |
| 7β-propargylthioacetamido-7α-methoxy-3-(1-methyl-1H-tetrazol-5-yl)thiomethyl-3-cephem-4-carboxylic acid | 0.2 | 0.8 | 3.1 | 3.1 | 3.1 | 3.1 | 400 | 3.1 | 0.8 |
| 7β-cyanomethylthioacetamido-7α-methoxy-3-(1-methyl-1H-tetrazol-5-yl)thiomethyl-3-cephem-4-carboxylic acid | 0.2 | 0.8 | 0.8 | 0.8 | 0.8 | 0.8 | >200 | 1.5 | 0.2 |
| 7β-(5-methyl-1,3,4-thiadiazol-2-yl)thio-acetamido-7α-methoxy-3-(1-methyl-1H-tetrazol-5-yl)thiomethyl-3-cephem-4-carboxylic acid | 0.4 | 1.5 | 12.5 | 12.5 | 6.2 | 12.5 | 400 | 3.1 | 1.5 |
| 7β-(1,2,4-triazol-4H-3-yl)thioacetamido-7α-methoxy-3-carbamoyloxymethyl-3-cephem-4-carboxylic acid | 1.5 | 6.2 | 6.2 | 12.5 | 12.5 | 6.2 | >400 | 25 | 6.2 |
| 7β-(imidazol-2-yl)thioacetamido-7α-methoxy-3-carbamoyloxymethyl-3-cephem-4-carboxylic acid | ≦0.1 | 0.8 | 1.5 | 3.1 | 3.1 | 3.1 | >200 | 6.2 | 1.5 |
| 7β-(1,3,4-thiadiazol-2-yl)thioacetamido-7α-methoxy-3-carbamoyloxymethyl-3-cephem-4-carboxylic acid | 0.4 | 1.5 | 3.1 | 3.1 | 3.1 | 3.1 | >400 | 6.2 | 1.5 |
| 7β-(5-methyl-1,3,4-thiadiazol-2-yl)thio-acetamido-7α-methoxy-3-carbamoyloxymethyl-3-cephem-4-carboxylic acid | 0.8 | 3.1 | 6.2 | 6.2 | 12.5 | 6.2 | >200 | 6.2 | 3.1 |
| 7β-propargylthioacetamido-7α-methoxy-3-carbamoyloxymethyl-3-cephem-4-carboxylic acid | 0.8 | 1.5 | 3.1 | 3.1 | 6.2 | 3.1 | >400 | 6.2 | 1.5 |
| 7β-cyanomethylthioacetamido-7α-methoxy-3-carbamoyloxymethyl-3-cephem-4-carboxylic acid | 0.8 | 1.5 | 1.5 | 0.8 | 3.1 | 0.4 | >400 | 6.2 | 0.4 |
| 7β-cyanomethylthioacetamido-7α-methoxy-3-acetoxymethyl-3-cephem-4-carboxylic acid | 0.2 | 0.8 | 1.5 | 1.5 | 3.1 | 1.5 | >400 | 6.2 | 0.8 |
| 7β-azidomethylthioacetamido-7α-methoxy-3-acetoxymethyl-3-cephem-4-carboxylic acid | 0.4 | 0.8 | 6.2 | 6.2 | 6.2 | 6.2 | >200 | 3.1 | 1.5 |
| 7β-(1,3,4-thiadiazol-2-yl)thioacetamido-7α-methoxy-3-acetoxymethyl-3-cephem-4-carboxylic acid | 0.8 | 1.5 | 3.1 | 6.2 | 6.2 | 3.1 | >400 | 6.2 | 3.4 |
| 7β-propargylthioacetamido-7α-methoxy-3-acetoxymethyl-3-cephem-4-carboxylic acid | 0.8 | 3.1 | 3.1 | 6.2 | 6.2 | 6.2 | >400 | 6.2 | 1.5 |
| 7β-(imidazol-2-yl)thioacetamido-7α-methoxy-3-acetoxymethyl-3-cephem-4-carboxylic acid | 1.5 | 6.2 | 12.5 | 25 | 25 | 12.5 | >400 | 25 | 6.2 |
| 7β-(3-isoxazolyloxy)acetamido-7α-methoxy-3-acetoxymethyl-3-cephem-4-carboxylic acid | ≦0.1 | 0.8 | 6.2 | 6.2 | 12.5 | 6.2 | >400 | 12.5 | 3.1 |
| 7β-(3-isoxazolyl)thioacetamido-7α-methoxy-3-acetoxymethyl-3-cephem-4-carboxylic acid | 0.2 | 0.8 | 3.1 | 6.2 | 6.2 | 3.1 | >400 | 3.1 | 1.5 |
| 7β-methylsulfonylacetamido-7α-methoxy-3-(1-methyl-1H-tetrazole-5-yl)thiomethyl-3-cephem-4-carboxylic acid | 0.8 | 3.1 | 1.5 | 1.5 | 1.5 | 0.8 | 400 | 12.5 | 0.4 |

I A    Staphylococcus aureus 209p
I B    Staphylococcus aureus (CP and PC resistant)
II.A    E. coli NIHJ
II B    E. coli 609 (CER resistant)
III    Shigella flexneri Komagome
IV A    Klebsiella neumoniae 806
IV B    Klebsiella neumoniae 846 (CER resistant)
V    Proteus vulgaris
VI    Salmonella enteritidis Gaertner As shown above, the compounds obtained by this invention have excellent antimicrobial activities against broad pathogenic microorganisms. These compounds can be administered orally or parenterally, for example, in the shape of capsules, tablets, and injections and most preferably by means of injection. The dosage unit depends upon the age, disease and weight of the patients, but a usual dosage unit is in amounts from 100 to 3,000 mg/per day and it is adminstered three or four times a day. But, if necessary, more than the above amount can be used.

Also, 7β-haloacetamidocephalosporin and 6β-haloacetamidopenicillanic acid derivatives such as 7β-chloroacetamido-7α-methoxy-3-(1-methyl-1H-tetrazol-5-yl)thiomethyl-3-cephem-4-carboxylic acid or its ester are useful intermediates which can be transformed into valuable cephalosporin and penicillin derivatives having valuable antimicrobial activity by replacement of halogen atom with other radicals.

This invention will be illustrated by the following examples in detail, but these examples are not intended to limit the scope of the invention.

EXAMPLE 1

Methyl 7β-chloroacetamido-7α-methoxy-3-methyl-3-cephem-4-carboxylate

1. Phosphorus pentachloride (600 mg) was dissolved in chloroform (24 ml), to which was added qinoline (0.4 ml). To the resulting mixture was added methyl 7β-dichloroacetamido-3-methyl-3-cephem-4-carboxylate (536 mg). The reaction mixture was stirred for 1 hour and then chloroform was removed in vacuo. To the residue was added tetrahydrofuran (40 ml) and precipitates were filtered off. The resulting tetrahydrofuran solution of methyl 7β-(1', 2',2'-trichloroethylidenimino)-3-methyl-3-cephem-4-carboxylate can be used in the next reaction without purification. For isolation of the pure compound the solution was worked up as follows. The tetrahydrofuran solution was poured into 10 % dipotassium hydrogenphosphate solution and extracted with ethyl acetate. The extracts were washed with water, dried ($Na_2SO_4$) and evaporated under reduced pressure at 20°C to give 530 mg of methyl 7β-(1',2',2'-trichloroethylidenimino)-3-methyl-3-cephem-4-carboxylate as an oil. NMR($CDCl_3$) δ ppm: 2.17(3 H, singlet), 3.27 and 3.50(2H, AB-quartet, J=19 Hz), 3.83(3H, singlet), 5.10(1H, doublet, J=5 Hz), 5.55(1H, doublet, J=5 Hz), 6.42(1H, singlet).

A methanol solution of lithium methoxide prepared from lithium(60 mg) and methanol(5 ml) was added at −70°C to a solution of methyl 7β-(1',2',2'-trichloroethylidenimino)-3-methyl-3-cephem-4-carboxylate which was obtained above. The reaction mixture was stirred at −70°C for 30 minutes and treated with acetic acid(0.5 ml) to decompose the excess of lithium methoxide. The solution was poured into water and extracted with ethyl acetate. The extracts were washed with water, dried($Na_2SO_4$) and evaporated to afford 480 mg of methyl 7β-(2'-chloro-1'-methoxyethylidenimino)-7α-methoxy-3-methyl-3-cephem-4-cephem-4-carboxylate, m.p. 138°–139°C.

2. Methyl 7β-(2'-chloro-1'-methoxyethylidenimino)-7α-methoxy-3-methyl-3-cephem-4-carboxylate(50 mg) was dissolved in dry chloroform(4ml), to which were added quinoline(0.05 ml) and trimethylchlorosilane(0.2 ml). Nitrogen gas was bubbled into this solution for 3 hours. The solution was poured into water and extracted with chloroform. The extracts were washed with water, dried ($Na_2SO_4$) and evaporated under reduced pressure to afford 45 mg of methyl 7β-chloroacetamido-7α-methoxy-3-methyl-3-cephem-4-carboxylate, m.p. 123°–125°C. IR $\nu_{max}^{Nujol}$ cm$^{-1}$: 3380, 1790, 1730, 1680. NMR($CDCl_3$) δppm: 2.25(3H, singlet), 3.20(2H, singlet), 3.53(3H, singlet), 3.73(3H, singlet), 4.07(2H, singlet), 4.98(1H, singlet), 7.43(1H, singlet).

The same compound was also obtained as follows: methyl 7β-(2'-chloro-1'-methoxyethylidenimino)-7α-methoxy-3-methyl-3-cephem-4-carboxylate(50 mg) was dissolved in dry tetrahydrofuran(2 ml), to which were added quinoline(0.1 ml) and boron trifluoride etherate(0.25 ml). The reaction mixture was stirred at room temperature overnight, then poured into water and extracted with ethyl acetate. The extracts were washed with water, dried($Na_2SO_4$) and evaporated in vacuo. The residue was chromatographed on silica gel to give 18 mg of methyl 7β-chloroacetamido-7α-methoxy-3-methyl-3-cephem-4-carboxylate.

EXAMPLE 2 p-Bromophenacyl 7β-chloroacetamido-7α-methoxy-3-acetoxymethyl-3-cephem-4-carboxylate 1. A methanol solution of lithium methoxide prepared from lithium(21 mg) and methanol(2 ml) was added to a cooled solution(−70°C.) of p-bromophenacyl 7β-(1',2',2'-trichloroethylidenimino)-3-acetoxymethyl-3-cephem-4-carboxylate in tetrahydrofuran which was prepared from p-bromophenacyl 7β-dichloroacetamido-3-acetoxymethyl-3-cephem-4-carboxylate(290 mg), phosphorus pentachloride (180 mg) and quinoline(0.12 ml) according to the procedure of example 1. The reaction mixture was stirred at −70°C. for 30 minutes and treated with acetic acid(0.15 ml). The solution was poured into water and extracted with ethyl acetate. The extracts were washed with water, dried($Na_2SO_4$) and evaporated under reduced pressure to furnish 240 mg of p-bromophenacyl 7β-(2'-chloro-1'-methoxyethylidenimino)-7α-methoxy-3-cephem-4-carboxylate. NMR($CDCl_3$) δ ppm: 2.08(3H, singlet), 3.37 and 3.58(2H, AB-quartet, J=19 Hz), 3.47(3H, singlet), 3.83(3 H, singlet), 4.17 and 4.50(2H, AB-quartet, J=13 Hz), 5.03(2H, AB-quartet, J=13 Hz), 5.05(1H, singlet), 5.43 and 5.57(2H, AB-quartet, J=16 Hz), 7.4–8.1(4H, multiplet). IR $\nu_{max}^{Nujol}$ cm$^{-1}$: 1780, 1740, 1700.

2. p-Bromophenacyl 7β-(2'-chloro-1'-methoxyethylidenimino)-7α-methoxy-3-acetoxymethyl-3-cephem-4-carboxylate(280 mg) was dissolved in dry chloroform(16 ml), to which were added quinoline(0.2 ml) and trimethylchlorosilane(0.8 ml). The reaction mixture was stirred at room temperature for 3 hours while nitrogen gas was introduced to the solution. The mixture was poured into water and extracted with chloroform. The extracts were washed with 10 % sodium dihydrogenphosphate solution and water, dried over magnesium sulfate and evaporated under reduced pressure to give 250 mg of p-bromophenacyl 7β-chloroacetamido-7α-methoxy-3-acetoxymethyl-3-cephem-4-carboxylate. NMR($CDCl_3$) δ ppm: 2.10(3H, singlet), 3.38 and 3.57(2H, AB-quartet, J=18 Hz), 3.58(3H, singlet), 4.13(2H, singlet), 5.05 and 5.13(2H, AB-quartet, J=14 Hz), 5.12(1H, singlet), 5.50(2H, singlet), 7.5–8.0(4H).

EXAMPLE 3

Benzhydryl 7β-chloroacetamido-7α-methoxy-3-acetoxymethyl-3-cephem-4-carboxylate

1. A methanol solution of lithium methoxide prepared from lithium (40 mg) and methanol(4 ml) was added to a cooled solution (−70°C.) of benzhydryl 7β-(1',2',2'-trichloroethylidenimino)-3-acetoxymethyl-3-cephem-4-carboxylate in tetrahydrofuran which was prepared from benzhydryl 7β-dichloroacetamido-3-acetoxymethyl-3-cephem-4-carboxylate(549 mg), phosphorus pentachloride(400 mg) and quinoline(0.27 ml) as described in Example 1. The reaction mixture was stirred at −70°C. for 30 minutes and treated with acetic acid(0.4 ml). The solution was poured into water and extracted with ethyl acetate. The combined extracts were washed with water, dried($Na_2SO_4$) and evaporated under reduced pressure to afford 480 mg of benzhydryl 7β-(2'-chloro-1'-methoxyethylideimino)-7α-methoxy-3-acetoxymethyl-3-cephem-4-carboxylate. NMR(CDCl$_3$) δ ppm: 2.05(3H, singlet), 3.27 and 3.45 (2H, AB-quartet, J=18 Hz), 3.42(3H, singlet), 3.77(3H, singlet), 4.10 and 4.45(2H, AB-quartet, J=16 Hz) 4.65 and 4.88(2H, AB-quartet, J=13 Hz), 4.94(1H, singlet), 6.85(1H, singlet), 7.0–7.6(10H, multiplet).

2. Quinoline(0.1 ml) and trimethylchlorosilane (0.5 ml) were added to a solution of benzhydryl 7β-(2'-chloro-1'-methoxyethylidenimino)-7α-methoxy-3-acetoxymethyl-3-cephem-4-carboxylate(270 mg) in dry chloroform (12 ml). Nitrogen gas was bubbled into this solution at room temperature for 1 hour. After the addition of trimethylchlorosilane(0.5 ml) introduction of nitrogen gas was continued further for 2 hours. The solution was poured into water and extracted with chloroform. The combined extracts were washed with water, dried(Na$_2$SO$_4$) and evaporated. The residue was chromatographed on silica gel to afford 230 mg of benzhydryl 7β-chloroacetamido-7α-methoxy-3-acetoxymethyl-3-cephem-4-carboxylate. NMR(CDCl$_3$) δ ppm: 1.97(3H, singlet), 3.30 and 3.40(2H, AB-quartet, J=17 Hz), 4.08(3H, singlet), 4.87(2H, singlet), 5.02 and 5.07(2H, AB-quartet, J=14 Hz), 5.04(1H, singlet), 6.95(1 H, singlet), 7.2–7.6(10H, multiplet).

EXAMPLE 4

Benzhydryl 7β-chloroacetamido-7α-methoxy-3-(1-methyl-1H-tetrazole-5-yl)thiomethyl-3-cephem-4-carboxylate 1. A tetrahydrofuran solution of benzhydryl 7β-(1', 2',2'-trichloroethylidenimino)-3-(1-methyl-1H-tetrazole-5-yl)thiomethyl-3-cephem-4-carboxylate which was prepared from benzhydryl 7-dichloroacetamido-3-(1-methyl-1H-tetrazole-5-yl)thiomethyl-3-cephem-4-carboxylate (314 mg), phosphorus pentachloride(180 mg) and quinoline (0.13 ml) according to the procedure of Example 1 was cooled to −78°C. To this solution was added a methanol solution of lithium methoxide prepared from lithium(24 mg) and methanol(2 ml). The reaction mixture was stirred at −78°C for 30 minutes and treated with acetic acid(0.25 ml). The solution was poured into water and extracted with ethyl acetate. The extracts were washed with water, dried(-Na$_2$SO$_4$) and evaporated under reduced pressure. The residue was purified by chromatograaphy on silica gel to give 220 mg of benzhydryl 7β-(2'-chloro-1'-methoxyethylidenimino)-7α-methoxy-3-(1-methyl-1H-tetrazole-5-yl)thiomethyl-3-cephem-4-carboxylate as powder. IR $\nu_{max}^{Nujol}$ cm$^{-1}$: 1775, 1730, 1650. NMR(CDCl$_3$) δ ppm: 3.38(3H, singlet), 3.50 and 3.60(2H, AB-quartet, J=18 Hz), 3.70(3H, singlet), 3.73(3 H, singlet), 4.08 and 4.22(2H, AB-quartet, J=7 Hz), 4.12 and 4.43(2H, AB-quartet, J=12 Hz), 4.96(1H, singlet), 6.86(1H, singlet), 7.15–7.45(10H, multiplet).

2. Benzhydryl 7β-(2'-chloro-1'-methoxyethylidenimino)-7α-methoxy-3-(1-methyl-1H-tetrazole-5-yl)thiomethyl-3-cephem-4-carboxylate(120 mg) was dissolved in chloroform 4 ml, to which were added quinoline(0.05 ml) and trimethylclorosilane(0.5 ml). The reaction mixture was stirred at room temperature(10°C.) overnight, poured into water, and extracted with chloroform. The extracts were washed with water, dried(Na$_2$SO$_4$) and evaporated under diminished pressure. The residue was chromatographed on silica gel to give 80 mg of benzhydryl 7β-chloroacetamido-7α-methoxy-3-(1-methyl-1H-tetrazole-5-yl)thiomethyl-3-cephem-4-carboxylate. IR $\nu_{max}^{Nujol}$ cm$^{-1}$: 1770, 1730, 1650. NMR(CDCl$_3$) δ ppm: 3.47 and 3.57(2H, AB-quartet, J=18 Hz), 3.52(3H, singlet), 3.78(3H, singlet), 4.07(2H, singlet), 4.27 and 4.42(2H AB-quartet, J=12 Hz), 5.01(1H, singlet), 6.88(1H, singlet), 7.15–7.50(10H, multiplet).

EXAMPLE 5

7β-Chloroacetamido-7α-methoxy-3-methyl-3-cephem-4-carboxylic acid

Trimethylchlorosilane(0.5 ml) and triethylamine (0.17 ml) were added to a solution of 7-dichloroacetamido-3-methyl-3-cephem-4-carboxylic acid(325 mg) in chloroform (12 ml). The reaction mixture was stirred at 10°C. overnight to afford a chloroform solution of 7-dichloroacetamido-3-methyl-3-cephem-4-carboxylic acid trimethylsilyl ester. The resulting solution was added dropwise at −50°C. to a mixture prepared from phosphorus pentachloride(220 mg), quinoline(0.15 ml) and chloroform (15 ml). The reaction mixture was stirred at −50°C. for 3 hours and diluted with dry tetrahydrofuran(20 ml). To this solution was added a methanol solution of lithium methoxide prepared from lithium(150 mg) and methanol(15 ml) a −78°C. The mixture was stirred at −78°C. for 30 minutes and treated with acetic acid(1.5 ml). The solution was poured into water and extracted with chloroform. The extracts were washed with water, dried(Na$_2$SO$_4$) and evaporated under reduced pressure. The residue was dissolved in a small amount of chloroform, to which was added excess hexane to precipitate the desired substance. This process was repeated three times to give 240 mg of 7β-(2'-chloro-1'-methoxyethylidenimino)-7α-methoxy-3-methyl-3-cephem-4-carboxylic acid. NMR(CDCl$_3$) δ ppm: 2.05(3H, singlet), 3.03 and 3.43(2H, AB-quartet, J=18 Hz), 3.40(3H, singlet), 3.75(3H, singlet), 4.18 and 4.53(2H, AB-quartet, J=12 Hz), 5.00(1H, singlet).

1'. 7-Dichloroacetamido-3-methyl-3-cephem-4-carboxylic acid(325 mg) was suspended in dry chloroform (5 ml), to which were added triethylamine(0.17 ml) and acetyl chloride(0.085 ml). The reaction mixture was stirred under cooling with ice-water for 1 hour to give the corresponding anhydride. The resulting solution was added at −22°C. to a mixture prepared by the addition of quinoline(0.18 ml) to a solution of phosphorus pentachloride(271 mg) in chloroform. The reaction mixture was stirred at −22°C. for 3 hours. To the resulting solution was added a methanol solution of lithium methoxide prepared from lithium(80 mg) and methanol(7 ml) at −22°C. The mixture was stirred at −22°C. for 10 minutes, treated with acetic acid(0.8 ml), poured into water and extracted with chloroform. The extracts were washed with water, dried(Na$_2$SO$_4$) and evaporated to furnish 300 mg of 7β-(2'-chloro-1'-methoxyethylidenimino)-7α-methoxy-3 -methyl-3-cephem-4-carboxylic acid as a crude product. This compound can be used in the next reaction without purification. A pure sample can be obtained according to the procedure of Example 5 - (1).

By substituting acetyl chloride for monochloroacetyl chloride in this example there was obtained the same compound.

2. Trimethylchlorosilane(1 ml) was added to a solution of 7β-(2'-chloro-1'-methoxyethylidenimino)-7α-methoxy-3-methyl-3-cephem-4-carboxylic acid(300 mg) in dry chloroform(10 ml). The reaction mixture was stirred at room temperature overnight. The solution was poured into water and extracted with ethyl acetate. The organic solution was extracted with a buffer solution of sodium dihydrogenphoshate and dipotassium hydrogenphosphate (pH 7.5). The aqueous extracts were acidified with 5N-hydrochloric acid to pH 2 and again extracted with ethyl acetate. The extracts were washed with water, dried ($Na_2SO_4$) and evaporated under reduced pressure to give 240 mg of 7β-chloroacetamido-7α-methoxy-3-methyl-3-cephem-4-carboxylic acid as powder. IR $\mu_{max}^{Nujol}$ cm$^{-1}$: 3250, 1765, 1695. NMR($CDCl_3$) δ ppm: 2.20(3H, single), 3.23(2H, singlet), 3.55(3H, singlet), 4.13(2H, singlet), 5.06 (1H, singlet), 7.70(1H, singlet), 8.62(1H, singlet).

EXAMPLE 6

7β-Chloroacetamido-7α-methoxy-3-acetoxymethyl-3-cephem-4-carboxylic acid

1. Trimethylchlorosilane(0.4 ml) and triethylamine (0.17 ml) were added to a solution of 7-dichloroacetamido-3-acetoxymethyl-3-cephem-4-carboxylic acid(383 mg) in chloroform(12 ml). The reaction mixture was stirred at room temperature for 1.5 hours to give 7-dichloroacetamido-3-acetoxymethyl-3-cephem-4-carboxylic acid trimethyl silylester. The resulting solution as added a −50°C. to a mixture prepared from phosphorus pentachloride(220 mg), quinoline(0.15 ml) and chloroform(15 ml). The mixture was stirred at −50°C. for 3 hours and diluted with tetrahydrofuran(20 ml). To the resulting solution was added a methanol solution of lithium methoxide prepared from lithium (150 mg) and methanol(15 ml) at −78°C. The reaction mixture was stirred at −78°C. for 30 minutes and treated with acetic acid(1.5 ml). The solution was poured into wate and extracted with chloroform. The extracts were washed with water, dried ($Na_2SO_4$) and evaporated. The residue was dissolved in a small amount of chloroform, to which was added excess hexane to precipitate the desired product. This process was repeated three times to give 320 mg of 7β-(2'-chloro-1'-methoxyethylidenimino)-7α-methoxy-3-acetoxymethyl-3-cephem-4-carboxylic acid. NMR($CDCl_3$) δ ppm: b 2.05(3H, singlet), 3.2–3.7(2H), 3.44(3H, singlet), 3.78(3H, singlet), 4.13 and 4.46(2H, AB-quartet, J=13 Hz), 4.8–5.2(2H), 5.02 (1H, singlet).

2. Trimethylchlorosilane(1 ml) was added to a solution of 7β-(2'-chloro-1'-methoxyethylidenimino)-7α-methoxy-3-acetoxymethyl-3-cephem-4-carboxylic acid(280 mg) in dry chloroform(10 ml). The reaction mixture was stirred at room temperature overnight, then poured into water and extracted with ethyl acetate. The organic solution was extracted with a buffer solution of sodium dihydrogenphosphate and dipotassium hydrogephosphate (pH 7.5). The aqueous extracts were acidified to pH 2 with 5N-hydrochloric acid solution and extracted with ethyl acetate. The combined extracts were washed with water, dried($Na_2SO_4$) and evaporated under diminished pressure to give 260 mg of 7β-chloroacetamido-7α-methoxy-3-acetoxymethyl-3-cephem-4-carboxylic acid as powder. NMR($CDCl_3$) δ ppm: 2.07(3H, singlet), 3.38 and 3.58(2H, AB-quartet, J=18 Hz), 3.62(3H, singlet), 4.18(2H, singlet), 5.00 and 5.19(2H, AB-quartet, J−15 Hz), 5.15(1H, singlet), 7.70(1H, singlet).

EXAMPLE 7

7β-Chloroacetamido-7α-methoxy-3-(1-methyl-1H-tetrazole-5-yl)thiomethyl-3-cephem-4-carboxylic acid 1. Trimethylchlorosilane(0.32 ml) and triethylamine (0.14 ml) were added to a solution of 7-dichloroacetamido-3-(1-methyl-1H-tetrazole-5-yl)thiomethyl-3-cephem-4-carboxylic acid(374 mg) in chloroform(10 ml) and the reaction mixture was stirred at 5 − 7°C. for 1.5 hours to give 7-chloroacetamido-3-(1-methyl-1H-tetrazole-5-yl) thiomethyl-3-cephem-4-carboxylic acid trimethylsilyl ester. The resulting solution was added to a mixture of phosphorus pentachloride(176 mg), quinoline(0.12 ml) and chloroform(15 ml) at −50°C. The reaction mixture was stirred at −50°C for 3 hours and diluted with tetrahyrofuran(20 ml), which was cooled to −78°C. To this solution was added a methanol solution of lithium methoxide prepared from lithium(140 mg) and methanol (15 ml) at −78°C. The mixture was stirred at −78°C. for 30 minutes and treated with acetic acid(1.2 ml). The solution was poured into water and extracted with chloroform. The chloroform solution was washed with water, dried ($Na_2SO_4$) and evaporated to give a residue. The aqueous layer in the extraction of chloroform was again extracted with ethyl acetate. The extracts were washed with water, dried ($Na_2SO_4$) and the solvent was removed by distillation under reduced pressure to afford a residue. The residual fractions obtained above were combined and dissolved in a small amount of chloroform, to which was added excess hexane to precipitate the desired product. This precipitation process was repeated three times to give 200 mg of pure 7β-(2'-chloro-1'-methoxyethylidenimino)-7α-methoxy-3-(1-methyl-1H- tetrazole-5-yl)thiomethyl-3-cephem-4-carboxylic acid. NMR($CDCl_3$) δ ppm: 3.38 and 3.56(2H, AB-quartet, J=19 Hz), 3.46(3H, singlet), 3.78(3H, singlet), 3.82(3H, singlet), 4.20 and 4.55(2H, AB-quartet, J=12 Hz), 4.47(2H, singlet), 5.07(1H, singlet).

1. 7-Dichloroacetamido-3-(1-methyl-1H-tetrazole-5-yl)thiomethyl-3-cephem-4-carboxylic acid(435 mg) was suspended in dry chloroform(5 ml), to which were added triethylamine(0.17 ml) and acetyl chloride(0.085 ml). The reaction mixture was stirred under cooling with ice-water for 1 hour. The resulting solution was diluted with chloroform(14 ml) and quinoline(0.18 ml), which was cooled to −22°C, followed by the addition of phosphorus pentachloride(271 mg). The mixture was stirred at −22°C. for 3 hours, then cooled to −78°C. and diluted with tetrahydrofuran(20 ml). To the resulting solution was added a methanol solution of lithium methoxide prepared from lithium(80 mg) and methanol(7 ml) at −78°C. The reaction mixture was stirred at the same temperature for 20 minutes and treated with acetic acid(0.8 ml). The solution was poured into water and extracted with chloroform. The extracts were washed with water, dried($Na_2SO_4$) and evaporated under reduced pressure to afford 370 mg of 7β-(2'-chloro-1'-methoxyethylidenimino)-7α-methoxy-3-(1-methyl-1H-tetrazol-5-yl)thiomethyl-3-cephem-4-carboxylic acid as a crude product. This product can be submitted to the next reaction. A pure sample was obtained by dissolving the crude product in a small amount of chloroform and by adding hexane to precipitate the desired substance.

In this example the addition of lithium methoxide in methanol was carried out at −22°C. instead of −78°C. to give the same result.

1″. 7-Dichloroacetamido-3-(1-methyl-1H-tetrazol-5-yl)thiomethyl-3-cephem-4-carboxylic acid(435 mg) was suspended in dry chloroform(5 ml), to which were added triethylamine(0.17 ml) and monochloroacetyl chloride (0.8 ml). The reaction mixture was stirred under cooling with ice-water for 1 hour. Then by following the procedure of example 7 - (1)' 350 mg of 7β-(2'-chloro-1'-methoxyethylidenimino)-7α-methoxy-3-(1-methyl)-1H-tetrazol-5-yl)thiomethyl-3-cephem-4-carboxylic acid was obtained as a crude product.

2. Trimethylchlorosilane(1 ml) was added to a solution of 7β-(2-'-chloro-1'-methoxyethylidenimino)-7α-methoxy-3-(1-methyl-1H-tetrazol-5-yl)thiomethyl-3-cephem-4-carboxylic acid(300 mg) in chloroform(10 ml). The reaction mixture was stirred at room temperature (about 10°C.) overnight, then poured into water and extracted with ethyl acetate. The organic solution was extracted with disodium hydrogenphosphate solution(pH 8). The aqueous extracts were acidified to pH 2 with 5N-hydrochloric acid solution and again extracted with ethyl acetate. The extracts were washed with water, dried ($Na_2SO_4$) and evaporated to give 250 mg of 7β-chloroacetamido-7α-methoxy-3-(1-methyl-1H-tetrazol-5-yl)thiomethyl-3-cephem-4-carboxylic acid as an amorphous solid. NMR($CD_3CN + D_2O$) δ ppm: 3.44(3H, singlet), 3.28 and 3.60(2H, AB-quartet, J=18 Hz), 3.87(3H, singlet), 4.11(2H, singlet), 4.30(2H, singlet), 5.01(1H, singlet). IR $\nu_{max}^{KBr}$ cm$^{-1}$: 1760, 1680, 1605.

EXAMPLE 8

7β-Chloroacetamido-7α-methoxy-3-(1-methyl-1H-tetrazol-5-yl)thiomethyl-3-cephem-4-carboxylic acid 1. 7-Dichloroacetamido-3-(1-methyl-1H-tetrazol-5-yl)thiomethyl-3-cephem-4-carboxylic acid(6.6 g) was suspended in anyhdrous chloroform(300 ml). The suspension was made to a homogeneous solution by addition of triethylamine (2.5 ml). To the solution was added trimethylchlorosilane (5.7 ml). The mixture was stirred for 30 minutes and allowed to stand at room temperature overnight. After addition of quinoline(4.5 ml), the mixture was cooled to −50°C, followed by addition of phosphorus pentachloride (3.8 g) and stirred at −50°C. for 3.5 hours. The solution became clear. To the solution was added dry tetrahydrofuran (100 ml). After cooling to −70°C, the mixture was stirred at −60° −−70°C. for 30 minutes with a methanol solution of lithium methoxide prepared from lithium(1.5 g) and methanol(120 ml), followed by addition of acetic acid (6.5 ml) in tetrahydrofuran(15 ml). The solvent was distilled under reduced pressure to give a crude product of 7β-(2'-chloro-1'-methoxyethylideneimino-7α-methoxy-3-(1-methyl-1H-tetrazol-5-yl)thiomethyl-3-cephem-4-carboxylic acid which was used directly in the next step.

2. The crude product obtained above was suspended in anhydrous chloroform(200 ml), followed by addition of trimethylchlorosilane(30 ml). The mixture was stirred at room temperature overnight and the solvent was distilled off under reduced pressure. The residue was extracted with phosphate buffer (pH 7.8), the extracts were washed with ethyl acetate, adjusted to pH 2.1 by addition of dilute hydrochloric acid and extracted with ethyl acetate. The extracts were washed with water, dried and evaporated to dryness under reduced pressure. The residue was dissolved in a small amount of ethyl acetate and the solution was added to hexane. The produced pricipitates were collected by filtration to give 4.6 g of the desired product.

EXAMPLE 9

7β-Chloroacetamido-7α-methoxy-3-(1-methyl-1H-tetrazol-5-yl)thiomethyl-3-cephem-4-carboxylic acid 1. 7-Dichloroacetamido-3-(1-methyl-1H-tetrazol-5-yl)thiomethyl-3-cephem-4-carboxylic acid (8.8 g) was suspended in anhydrous chloroform(400 ml). The suspension was made to a homogeneous solution by addition of triethylamine(3.3 ml). To the solution was added dichlorodimethylsilane(2.4 ml). The mixture was stirred for 2 hours at room temperature. After addition of quinoline (6 ml), the mixture was cooled to −50°C, followed by addition of phosphorus pentachloride(5.0 g) and stirred at −50°C. for 3.5 hours. The solution became clear. To the solution was added dry tetrahydrofuran(100 ml). After cooling to −70°C, the mixture was stirred at −60° −−70°C. for 30 minutes with a methanol solution of lithium methoxide prepared from lithium(2.0 g) and methanol(150 ml), followed by addition of acetic acid (8.7 ml) in tetrahydrofuran(15 ml). The solvent was distilled under reduced pressure to give a crude product of 7β-(2'-chloro-1'-methoxyethylideneimino)-7α-methoxy-3-(1-methyl-1H-tetrazole-5-yl)thiomethyl-3-cephem-4-carboxylic acid which was used directly in the next step.

2. The crude product obtained above was suspended in anhydrous chloroform(270 ml), followed by addition of dichlorodimethylsilane(40 ml). The mixture was stirred at room temperature overnight and the solvent was distilled off under reduced pressure. The residue was extracted with phosphate buffer(pH 7.8), which was washed with ethyl acetate, adjusted to pH 2.1 by addition of dilute hydrochloric acid and extracted with ethyl acetate. The extracts were washed with water, dried and evaporated to dryness under reduced pressure. The residue was dissolved in a small amount of ethyl acetate and the solution was added to hexane. The produced pricipitates were collected by filtration to give 6.6 g of the desired product.

EXAMPLE 10

7β-Chloroacetamido-7α-methoxy-3-(1-methyl-1H-tetrazole-5-yl)thiomethyl-3-cephem-4-carboxylic acid 1. 7-Dichloroacetamido-3-(1-methyl-1H-tetrazol-5-yl)thiomethyl-3-cephem-4-carboxylic acid(1.32 g) was suspended in anhydrous chloroform(18 ml). Triethylamine (0.85 ml) was added to the mixture under ice-cooling, followed by stirring for 5 minutes. Phosphorus trichloride(0.27 ml) was added to the mixture and stirred under ice-cooling for 30 minutes. Afer cooling to −20°C, dry quinoline(1.42 ml) and phosphorus pentachloride(1.26 g) were added the mixture, followed by stirring for 2 hours at −20°C. Dry tetrahydrofuran(18 ml) was added to the mixture which was then cooled with dry ice-acetone. A methanol solution of lithium methoxide prepared from lithium (315 mg) and methanol(25 ml) was mixture to the mixture maintaining the internal temperature below −50°C, followed by stirring for one hour. Acetic acid (3 ml) was added to the mixture and stirred for 10 minutes. The solvent was distilled off under reduced pressure. The residue was dissolved in anhydrous chloroform(30 ml) and the solution was evaporated to dryness under reduced pressure. The residue obtained was suspended in anhydrous chloroform(30 ml) to which was added trimethylchlorosilane (6 ml), followed by stirring at room temperature overnight. The solvent was distilled off under reduced pressure. Ethyl acetate(100 ml) and water(50 ml) ere added to the residue and the mixture was agitated vigorously. The separated aqueous layer was extracted with ethyl acetate (100 ml). The combined extracts were re-extracted four times with 50 ml of a buffer solution (pH 7.5, 10 % $KH_2PO_4$ : 10 % $Na_2HPO_4$ = 5 : 1). The aqueous layer was adjusted to pH 2.0 by addition of 10 % HCl with ice-water cooling. The mixtuure was saturated with sodium chloride. The solution was extracted three time with ethyl acetate (100 ml). The combined extracts were dried over sodium sulfate and the solvent was distilled off. To the residue was added ether(5 ml). The mixture was washed with n-hexane(10 ml) and the solvent was removed by decantation. The residue was dried under reduced pressure to give 450 mg of the desired product as pale yellow powder.

EXAMPLE 11 p-Bromophenacyl 7β-methylthioacetamido-7α-methoxy-3-acetoxymethyl-3-cephem-4-carboxylate 1. A methanol solution of lithium methoxide prepaed from lithium(35 mg) and methanol(3 ml) was added at −70°C. to a tetrahydrofuran solution of p-bromophenacyl 7β-(1'-chloro-2'-methylthio-2'-bromoethylidenimino)-3-acetoxymethyl-3-cephem-4-carboxylate which was prepared from p-bromophenacyl 7β-(2'-methylthio-2'-bromoacetamido)-3-acetoxymethyl-3-cephem-4-carboxylate(330 mg), phosphorus pentachloride(180 mg) and quinoline(0.13 ml) according to the procedure of Example 1. The reaction mixture was stirred at −70°C. for 30 minutes and treated with acetic acid(0.25 ml). The solution was poured into water and extracted with ethyl acetate. The extracts were washed with water, dried ($Na_2SO_4$) and evaporated under diminished pressure. The residue was purified by chromatography on silica gel to give 120 mg of p-bromophenacyl 7β-(1'-methoxy-2'-methylthioethylidenimino)-7α-methoxy-3-acetoxymethyl-3-cephem-4-carboxylate. NMR($CDCl_3$) δ ppm: 2.05(3H, singlet), 2.18(3 H, singlet), 3.45(3H, singlet), 3.3–3.9(4H, two kinds of AB-quartet), 3.78(3H, singlet), 5.02(2H and 1H), 5.45–5.55(52H, AB-quartet), 7.55–7.90(4H, multiplet).

2. Quinoline(0.1 ml) and trimethylchlorosilane (0.5 ml) were added to a solution of p-bromophenacyl 7β-(1'-methoxy-2'-methylthioethylidenimino)-7α-methoxy-3-acetoxymethyl-3-cephem-4-carboxylate(100mg) in dry chloroform(10 ml). The reaction mixture was stirred at room temperature overnight. The solution was poured into water and extracted with ethyl acetate. The extracts were washed with water, dried($Na_2SO_4$) and evaporated under reduced pressure to give 80 mg of p-bromophenacyl 7β-methylthioacetamido-7α-methoxy-3-acetoxymethyl-3-cephem-4-carboxylate, IR $\nu_{max}^{liquid}$ cm$^{-1}$: 1780, 1740, 1705.

EXAMPLE 12 p-Bromophenacyl 7β-phenylthioacetamido-7α-methoxy-3-acetoxymethyl-3-cephem-4carboxylate 1. A methanol solution of lithium methoxide prepared from lithium(24 mg) and methanol(2 ml) was added at −70°C. to a tetrahydrofuran solution of p-bromophenacyl 7-(2'-phenylthio-2'-bromo-1'-chloroethylidenimino)-3-acetoxymethyl-3-cephem-4-carboxylate which was prepared from p-bromophenacyl 7-(2'-phenylthio-2'-bromoacetamido)-3-acetoxymethyl-3-cephem-4-carboxylate(350 mg), phosphorus pentachloride(180 mg) and quinoline (0.13 ml) according to the procedure of Example 1. The reaction mixture was stirred at −70°C. for 30 minutes and treated with acetic acid(0.25 ml). The solution was poured into water and extracted with ethyl acetate. The extracts were washed with water, dried ($Na_2SO_4$) and evaporated under reduced pressure to afford 150 mg of p-bromophenacyl 7-(2'-phenylthio-1'-methoxyethylidenimino)-7α-methoxy-3-acetoxymethyl-3-cephem-4-carboxylate. IR $\nu_{max}^{liquid}$ cm$^{-1}$: 1770, 1735, 1700. NMR($CDCl_3$) δ ppm: 2.05(3 H, singlet), 3.30 and 3.55(2H, AB-quartet, J=18 Hz), 3.36(3H, singlet), 3.70(3H, singlet), 3.80 and 4.12(2H, AB-quartet, J=13 Hz), 4.90 and 5.07(2H, AB-quartet, J=14 Hz), 5.00(1H, singlet), 5.35 and 5.52(2H, AB-quartet, J=14 Hz), 7.0–7.4(5H), 7.4–7.9(4H).

2. Quinoline(0.05 ml) and trimethylchlorosilane (0.3 ml) were added to a solution of p-bromophenacyl 7-(2'-phenylthio-1'-methoxyethylidenimino)-7α-methoxy-3-acetoxymethyl-3-cephem-4-carboxlate(80 mg) in chloroform(5 ml). The reaction mixture was stirred at room temperature for 6 hours while nitrogen gas was introduced to the solution. After pouring into water the mixture was extracted with chloroform. The extracts were washed with water, dried($Na_2SO4$) and evaporation under reduced pressure. The residue was chromatographed on silica gel to give 55 mg of p-bromophenacyl 7β-phenylthioacetamido-7α-methoxy-3-acetoxymethyl-3-cephem-4-carboxylate. NMR($CDCl_3$) δ ppm: 2.08(3H, singlet), 3.27 and 3.40(2H, AB-quartet, J=18 Hz), 3.37(3H, singlet), 3.68(2H, singlet), 5.05(2H and 1H), 5.46(2H), 7.2–7.4(5H, multiplet), 7.6–7.8(4H, multiplet).

EXAMPLE 13 p-Bromophenacyl 7β-(2'-α-thienylacetamido)-7α-methoxy-3-acetoxymethyl-3-cephem-4-carboxylate 1. A methanol solution of lithium methoxide prepared from lithium(24 mg) and methanol(2 ml) was added at −70°C. to a tetrahydrofuran solution of p-bromophenacyl 7β-(1',2'-dichloro-2'-α-thienylethylidenimino)-3-acetoxymethyl-3-cephem-4-carboxylate which was prepared from p-bromophenacyl 7β-(2'-α-thienyl-2'-chloroacetamido)-3-acetoxymethyl-3-cephem-4-carboxylate(315 mg), phosphorus pentachloride(180 mg) and quinoline(0.13 ml) according to the procedure of Example 1. The reaction mixture was stirred at −70°C. for 30 minutes and treated with acetic acid(0.25 ml). The solution was poured into water and extracted with ethyl acetate. The extracts were washed with water, dried($Na_2SO_4$) and evaporated under reduced pressure. The residue was purified by silica gel chromatography to afford 160 mg of p-bromophenacyl 7β-(1'-methoxy-2'-α-thienylethylidenimino)-7α- methoxy-3-acetoxymethyl-3-cephem-4-carboxylate. IR $\nu_{max}^{Nujol}$ cm$^{-1}$: 1780, 1740, 1705, 1650. NMR(CDCl$_3$) δ ppm: 2.10(3H, singlet), 3.43(3H, singlet), 3.40 and 3.60(2H, AB-quartet, J=18 Hz), 3.77(3H, singlet), 4.03 and 4.30(2H, AB-quartet, J=15 Hz), 5.0–5.3(2H and 1H), 5.45–5.60(2H, AB-quartet), J=16 Hz), 6.9–7.4 (3H, multiplet), 7.5–7.9(4H, multiplet).

2. Quinoline(0.1 ml) and trimethylchlorosilane (0.5 ml) were added to a solution of p-bromophenacyl 7β-(1′-methoxy-2′-α-thienylethylidenimino)-7α-methoxy-3-acetoxymethyl-3-cephem-4-carboxylate(100 mg) in chloroform(10 ml). The reaction mixture was stirred at room temperature overnight, then poured into water and extracted with ethyl acetate. The extracts were washed with water, dried(Na$_2$SO$_4$) and evaporated under reduced pressure to afford 70 mg of p-bromophenacyl 7β-(2′-α-thienylacetamido)-7α-methoxy-3-acetoxymethyl-3-cephem-4-carboxylate. IR $\nu_{max}^{Nujol}$ cm$^{-1}$: 1780, 1740, 1700, 3330. NMR(CD$_3$COCD$_3$) δ ppm: 2.07(3H, singlet), 3.40 and 3.50(2H, AB-quartet, J=18 Hz), 3.45(3H, singlet), 3.87(2H, singlet), 5.01(2H), 5.04(1H, singlet), 5.45(2H, singlet), 6.5–7.5 (3H), 7.5–7.9(4H, A$_2$B2 type).

EXAMPLE 14

Methyl 6β-chloroacetamido-6α-methoxy-2,2-dimethylpenam-3-carboxylate

1. A methanol solution of lithium methoxide prepared from lithium(40 mg) and methanol(3 ml) was added at −70°C. to a tetrahydrofuran solution of methyl 6β-(1′,2′,2′-trichloroethylidenimino)-2,2-dimethylpenam-3-carboxylate which was prepared from methyl 6β-dichloroacetamido-2,2-dimethylpenam-3-carboxylate(300 mg), phosphorus pentachloride(300 mg) and quinoline(0.2 ml) by following the procedure of Example 1. The reaction mixture was stirred at −70°C. for 30 minutes and treated with acetic acid(0.5 ml). The solution was poured into water and extracted with ethyl acetate. The extracts were washed with water, dried(Na$_2$SO$_4$) and evaporated under reduced pressure. The residue was chromatographed on silica gel to give 170 mg of methyl 6β-(2′-chloro-1′-methoxyethylidenimino)-6α-methoxy-2,2-dimethylpenam-3-carboxylate. IR $\nu_{max}^{Nujol}$ cm$^{-1}$: 1775, 1745, 1650. NMR(CDCl$_3$) δ ppm: 1.45(3H, singlet), 1.52(3H, singlet), 3.50(3H, singlet), 3.78(3H, singlet), 3.82(3H, singlet), 4.10 and 4.37(2H, AB-quartet, J=13 Hz), 4.42(1H, singlet), 5.53(1H, singlet).

2. Quinoline(0.05 ml) and trimethylchlorosilane (0.5 ml) were added to a solution of methyl 6β-(2′-chloro-1′-methoxyethylidenimino)-6α-methoxy-2,2-dimethylpenam-3-carboxylate(100 mg) in dry chloroform(10 ml). The reaction mixture was stirred at 10°C. for 6 hours. After the addition of water the mixture was extracted with ethyl acetate. The extracts were washed with water, dried(Na$_2$SO$_4$) and evaporated under reduced pressure. The residue was chromatographed on silica gel to afford 45 mg of methyl 6β-chloroacetamido-6α-methoxy-2,2-dimethylpenam-3-carboxylate. IR$\nu_{max}^{Nujol}$ cm$^{-1}$: 3340, 1780, 1755, 1695. NMR(CDCl$_3$) δ ppm: 1.44(3H, singlet), 1.53(3H, singlet), 3.52(3H, singlet), 3.77(3H, singlet), 4.10(2H, singlet), 4.47(1H, singlet), 5.57(1H, singlet), 7.67(1H, broad singlet).

EXAMPLE 15

7β-Cyanomethylthioacetamido-7α-methoxy-3-(1-methyl-1H-tetrazole-5-yl)thiomethyl-3-cephem-4-carboxylic acid 1. To anhydrous chloroform(180 ml) were added 7-(2′-cyanomethylthio-2′-chloroacetamido)-3-(1-methyl-1H-tetrazole-5-yl)thiomethyl-3-cephem-4-carboxylic acid(6 g), trimethylamine(2.18 ml) and trimethylchlorosilane(4.8 ml). The mixture was stirred for 30 minutes and allowed to stand at room temperature overnight. After addition of quinoline(3.78 ml), the mixture was cooled to −50°C. and stirred at −50°C. for 3.5 hours with phosphorus pentachloride(3.42 g). After addition of dry tetrahydrofuran (60 ml), the clear solution was cooled to −78°C. and stirred at −78°C. for 25 minutes with a methanol solution of lithium methoxide prepared from lithium(1.2 g) and methanol(96 ml). To the reaction mixture was added acetic acid(5 ml) in tetrahydrofuran(15 ml). The temperature of the mixture was allowed to rise to room temperature under stirring. The solvent was distilled off under reduced pressure to give a crude product of 7β-(2′-cyanomethylthio- 1′-methoxyethylideneimino)-7α-methoxy-3-(1-methyl-1H-tetrazole-5-yl)thiomethyl-3-cephem-4-carboxylic acid, which could be used as a starting material in the next step without purification. Purification of the product, if desired, can be carried out as follows; water was added to the crude product and the mixture was extracted with ethyl acetate. The extracts were washed with water, dried and evaporated to dryness under reduced pressure.

The residue was dissolved in a small amount of ethyl acetate and precipitated with hexane to give 4.2 g of a pure desired product.

2. The crude product obtained above was suspended to dry chloroform(168 ml) and trimethylchlorosilane(25.2 ml) was added to the suspension. The mixture was stirred at room temperature overnight and evaporated to dryness under reduced pressure. To the residue was added water and extracted with ethyl acetate. The extracts were re-extracted with a phosphate buffer(pH 7.8). The extracts were adjusted to pH 2.1 with diluted hydrochloric acid and extracted with ethyl acetate. The extracts thus obtained were washed with water, dried and evaporated to dryness under reduced pressure. The residue was dissolved in a small amount of ethyl acetate, precipitated with hexane to give 3.6 g of 7β-cyanomethylthioacetamido-7α-methoxy-3-(1-methyl-1H-tetrazole-5-yl)thiomethyl-3-cephem-4-carboxylic acid. NMR(CD$_3$COCD$_3$) δ ppm: 3.50(3H, singlet), 3.60(2H, singlet), around 3.5–3.7(2H, quartet), 3.70(2H, singlet), 3.98(3H, singlet); 4.3–4.6(2H, quartet), 5.10(1H, singlet).

EXAMPLE 16

7β-Cyanomethylthioacetamido-7α-methoxy-3-acetoxymethyl-3-cephem-4-carboxylic acid Following the same procedure as in Example 15 (1), but replacing 7-(2′-cyanomethylthio-2′-chloroacetamido)-3-(1-methyl-1H-tetrazol-5-yl)thiomethyl-3-cephem-4-carboxylic acid with 7-(2′-cyanomethylthio-2′-chloroacetamido)-3-acetoxymethyl-3-cephem-4-carboxylic acid (5.3 g), there was obtained a crude product of 7β-(2′-cyanomethylthio-1′-methoxyethylideneimino-7α-methoxy- 3-acetoxymethyl-3-cephem-4-carboxylic acid. The crude product thus obtained was treated with the same procedure as in Example 15 - (2) to give 3.2 g of 7β-cyanomethylthioacetamido-7α-methoxy-3-acetoxymethyl-3-cephem-4-carboxylic acid. NMR(CD₃COCD₃) δ ppm: 207(3singlet), around 3.5(2H), 3.50(3H, singlet), 3.58(2H, singlet), 3.73(2H, singlet), 4.83 and 5.07(2H, AB-quartet, J=13 Hz), 5.11(1H, singlet).

EXAMPLE 17

7β-Methanesulfonylacetamido-7α-methoxy-3-(1-methyl- 1H-tetrazole-5-yl)thiomethyl-3-cephem-4-carboxylic acid 1. To anhydrous chloroform(12 ml) were added 7-(2'-methanesulfonyl-2'-bromoacetamido)-3-(1-methyl-1H-tetrazole-5-yl)thiomethyl-3-cephem-4-carboxylic acid (562 mg), triethylamine(0.17 ml) and trimethylchlorosilane (0.38 ml). The mixture was stirred for 30 minutes and allowed to stand at room temperature overnight. After addition of quinoline(0.6 ml), the mixture was cooled to −50°C. and stirred with phosphorus pentachloride(450 mg) at −50°C. for 3.5 hours. To the mixture was added dry tetrahydrofuran(20 ml). The mixture was cooled to −78°C. and stirred with a methanol solution of lithium methoxide prepared from lithium(110 mg) and methanol (10 ml) at −78°C. for 30 minutes, followed by addition of acetic acid (1 ml). After addition of water, the mixture was extracted with chloroform, washed with water, dried and evaporated to dryness under reduced ressure to give 670 mg of a crude product of 7β-(2'methanesulfonyl-1'methoxyethylideneimino)-7α-methoxy-3-(1-methyl-1H-tetrazole-5-yl)thiomethyl-3-cephem-4-carboxylic acid which could be used as a starting material in the next step without purification. The crude product, if necessary, can be purified by means of recrystalliation from a mixture of ethyl acetate and hexane.

Following the same procedure as above, but replacing 7-(2'-methanesulfonyl-2'-bromoacetamido-3-(1-methyl-1H-tetrazol-5-yl)thiomethyl-3-cephem-4-carboxylic acid with 7-(2'-methanesulfonyl-2'-chloroacetamido)-3-(1-methyl-1H-tetrazole-5-yl)thiomethyl-3-cephem-4-carboxylc acid, there was obtained the same product as above.

2. The crude product obtaned above was dissolved in anhydrous chloroform(15 ml) and the solution was stirred with trimethylchlorosilane(1 ml.) at room temperature overnight. The solvent was distilled off under reduced pressure. After addition of water, the mixture was extracted with ethyl acetate. The ethyl acetate extracts were re-extracted with a phosphate buffer(pH 7.8) and followed by adjusting to pH 2.1 with diluted hydrochloric acid. The solution was extracted with ethyl acetate. The extracts were washed with water, dried and evaporated to dryness under reduced pressure. The residue was dissolved in a small amount of ethyl acetate and precipitated by addition of hexane. This precipitation procedure was repeated three times to give 320 mg. of 7β-methanesulfonylacetamido-7α-methoxy-3-(1-methyl-1H-tetrazole-5-yl)thiomethyl-3-cephem-4-carboxylic acid. NMR(CD₃COCD₃) δ ppm: 3.07(3H, singlet), 3.45(3H, singlet), 3.62(2H, quartet), 3.92(3H, singlet), 4.18(2H, singlet), 4.35(2H, quartet), 5.06)1H, singlet), 8.60(1H, singlet).

Example 18

7β-Ethanesulfonylacetamido-7α-methoxy-3-(1-methyl-1H-tetrazole-5-yl)thiomethyl-3-cephem-4-carboxylic acid 1. Following the same procedure as in Example 17 (1), but replacing 7-(2'-methanesulfonyl-2'-bromoacetamido)-3-(1-methyl-1H-tetrazole-5-yl)thiomethyl-3-cephem-4-carboxylic acid with 7(2'-ethanesulfonyl-2'-bromoacetamido)-3-(1methyl-1H-tetrazole-5-yl)thiomethyl-3-cephem-4-carboxylic acid (0.58 g), there was obtained a crude product of 7β-(2'-ethanesulfonyl-1'-methoxyethylideneimino)-7α-methoxy-3-(1-methyl-1H-tetrazol-5-yl)thiomethyl-3-cephem-4-carboxylic acid which could be used as a starting material in the next step. The crude product thus obtained was treated with the same procedure as in Example 17 (2) to give 0.28 g of 7β-ethanesulfonylacetamido-7α-methoxy-3-(1methyl-1H-tetrazole-5-yl)thiomethyl-3-cephem-4-carboxylic acid.

EXAMPLE 19

Methyl 7β-cyanomethylthioacetamido-7α-methoxy-3-methyl-3-cephem-4-carboxylate

To anhydrous chloroform(10ml) were added successively phosphorous pentachloride (220 mg) and quinoline (0.17 ml). To the mixture was added methyl 7-(2'-cyanomethylthio-2'-bromoacetamido)-3-methyl-3-cephem-4-carboxylate(270 mg). The mixture was stirred at room temperature for 40 minutes and evaporated to dryness. To the residue was added dry tetrahydrofuran(50 ml). The mixture was filtered. The filtrate was cooled to −78°C. and stirred at −78°C. for 20 minutes with a methanol solution of lithium methoxide prepared from lithium(50 mg) and methanol(5 ml). To the reaction mixture was added water(2 ml) containing acetic acid (0.5 ml) to finish the reaction. After addition of saturated aqueous sodium chloride solution, the mixture was extracted with ethyl acetate. The extract was washed with water, dried and evaporated to dryness under reduced pressure to give 190 mg of methyl 7β-(2'-cyanomethylthio-1'-methoxyethylideneimino)-7α-methoxy-3-methyl-3-cephem-4-carboxylate. NMR(CDCl₃) δ ppm: 2.15(3H, singlet) 2.95 and 3.20(2H, AB quartet), 3.38(3H, singlet), 3.69(3H, singlet), 3.74 (3H, singlet), 3.5–3.8(4H), 4.93(1H, singlet).

2. To anhydrous chloroform(10 ml) were added successively methyl 7β-(2'-cyanomethylthio-1'-methoxyethylideneimino)-7α-methoxy-3-methyl-3-cephem-4-carboxylate(350 mg), quinoline(0.1 ml) and trimethylchlorosilane(1.0 ml). The mixture was allowed to stand at room temperature overnight and evaporated to dryness under reduced pressure. After addition of water, the residue was extracted with ethyl acetate. The extract was washed with water, dried and evaporated to dryness. The residue was purified by means of silica gel chromatography to give 280 mg of methyl 7β-cyanomethylthioacetamido-7α-methoxy-3-methyl-3-cephem-4-carboxylate. NMR(CDCl₃) δ ppm: 2.15(3H, singlet), 3.25(2H), 3.48 (2H, singlet), 3.54(5H, singlet), 3.82(3H, singlet), 5.06(1H, singlet), 7.87(1H, singlet).

EXAMPLE 20

Methyl 7β-methylsulfonyl-7α-methoxy-3-methyl-3-cephem-4-carboxylate

1. To anhydrous chloroform(10 ml) were added successively phosphorus pentachloride(310 mg) and quinoline (0.23 ml). To the mixture was added methyl 7-(2'-methanesulfonyl-2'-bromoacetamido)-3-methyl-3-cephem-4-carboxylate (350 mg). The mixture was stirred at room temperature for 50 minutes and evaporated to dryness. To the residue was added dry tetrahydrofuran(50 ml) and the mixture was filtered. The filtrate was cooled to −78°C. and stirred at −78°C. for 20 minutes with a methanol solution of lithium methoxide prepared from lithium(50 mg) and methanol (10 ml). To the reaction mixture was added water(2ml) containing acetic acid (0.4 ml) to finish the reaction. The mixture was poured into water saturated with sodium chloride and extracted with ethyl acetate. The extracts were washed with water, dried and evaporated under reduced pressure to give 320 mg of methyl 7β-(2'-methanesulfonyl-1'-methoxyethylideneimino)-7α-methoxy-3-methyl-3-cephem-4-carboxylate. The product can be purified by means of silica gel chromatography. NMR(CDCl$_3$) δ ppm: 2.04(3H, singlet), 3.06(3H, singlet), 2.9–3.5(2H), 3.44 (3H, singlet), 3.78(6H, singlet), 4.20 and 4.65(2H, AB quartet, J=14 Hz), 4.97(1H, singlet).

2. To chloroform(10 ml) were added successively methyl 7β-(2'-methanesulfonyl-1'-methoxyethylideneimino)-7α-methoxy-3methyl-3-cephem-4-carboxylate(300 mg), quinoline(0.1 ml) and trimethylchlorosilane(1 ml). The mixture was allowed to stand at room temperature overnight and evaporated to dryness. After addition of water, the residue was extracted with ethyl acetate. The extracts were washed with water, dried and vaporated to dryness under reduced pressure. The residue was purified by means of silica gel chromatography to give 240 mg of methyl 7β-methanesulfonyl-7α-methoxy-3-methyl-3-cephem-4-carboxylate. NMR(CDCl$_3$) δ ppm: 2.08(3H, singlet), 3.08 (3H, singlet), 3.19(2H), 3.49(3H, singlet), 3.76(3H, singlet), 4.07(2H, singlet), 4.97(1H, singlet), 8.33(1H, singlet).

EXAMPLE 21

7β-(α-Thienylacetamido)-7α-methoxy-3-(1-methyl-1H-tetrazole-5yl)thiomethyl-3-cephem-4-carboxylic acid 1. To dry chloroform(12ml) were added successively 7(2'-α-thienyl-2'-chloroacetamido)-3-(1-methyl-1H-tetrazole- 5-yl)thiomethyl-3-cephem-4-carboxylic acid (486 mg), triethylamine(0.17 ml) and trimethylchlorosilane (0.4 ml). The mixture was stirred at room temperature for 1 hour. To the mixture were added dry chloroform(16 ml) and quinoline(0.3 ml). The reaction mixture was cooled to −60°C. and stirred at −50°C. for 3.5 hours with phosphorus pentachloride(250 mg). After addition of dry tetrahydrofuran(20 ml), the mixture was cooled to −78°C. To the mixture was added a methanol solution of lithium methoxide prepared from lithium(100 mg) and methanol (10 ml). The mixture was stirred at −78°C. for 30 minutes, followed by addition of acetic acid(1.0 ml) to finish the reaction. After addition of water, the mixture was extracted with ethyl acetate. The extracts were washed with water, dried and evaporated to dryness under reduced pressure to give 520 mg of a crude product of 7β-(2'-α-thienyl-1'-methoxyethylideneimino)-7α-methoxy-3-(1-methyl-1H-tetrazole-5-yl)thiomethyl-3-cephem-4-carboxylic acid. The crude product was dissolved in a small amount of chloroform and precipitated with hexane to give a pure desired product. des 2. To chloroform(10 ml) were added successively 7β-(2'α-thienyl-1'-methoxyethylideneimino)-7α-methoxy-3-(1-methyl-1H-tetrazole-5-yl)thiomethyl-3-cephem-4-carboxylic acid(0.5 g), quinoline(0.12 ml) and trimethylchlorosilane(1.0 ml). The mixture was stirred at room temperature overnight. The reaction mixture was poured into water and extracted with chloroform. The extracts were re-extracted with a phosphate buffer(pH 7.5) and the aqueous layer was adjusted to pH 2 with 5N-hydrochloric acid, followed by extraction with ethyl acetate. The extracts were washed with water, dried and evaporated to give 0.4 g of 7β-(α-thienylacetamido)-7α-methoxy-3-(1-methyl-1H-tetrazole-5-yl)thiomethyl-3-cephem-4-carboxylic acid. NMR(CD$_3$COCD$_3$) δ ppm: 3.42(3H, singlet), 3.53 and 3.76(2H, AB doublet, J=18 Hz), 3.92(2H, singlet), 3.96(3H, singlet), 4.28 and 4.50(2H, AB doublet, J=14 Hz), 5.04(1 H, singlet), 6.8–7.1 (2H, multiplet), 8.27(1H, broad singlet).

EXAMPLE 22

Benzhydryl 7β-dichloroacetamido-7α-methoxy-3-acetoxymethyl-3-cephem-4-carboxylate 1. To a solution of phosphorus pentachloride(180 mg) in anhydrous chloroform(8 ml) were added under ice-cooling quinoline(0.13 ml) and then benzhydryl 7-trichloroacetamido-3-acetoxymethyl-3-cephem-4-carboxylate(291 mg). The mixture was stirred under ice-cooling for one hour and the solvent was distilled off under reduced pressure. To the residue was added anhydrous tetrahydrofuran(20 ml) and crystalline substances were filtered off. The filtrate was stirred at −78°C. for 20 minutes with a methanol solution of lithium methoxide prepared from lithium(24 mg) and methanol (2 ml), followed by addition of acetic acid (0.25 ml). The reaction mixture was poured into water, extracted with ethyl acetate, washed with water, dried and evaporated to dryness. The residue was purified by silica gel chromatography to give 30 mg of benzhydryl 7β-(2',2'-dichloro-1'-methoxethylideneimino)-7α-methoxy-3-acetoxymethyl-3-cephem-4-carboxylate. IR $\nu_{max}^{liquid\ film}$ cm$^{-1}$: 1770, 1730, 1650. NMR(CDCl$_3$) δ ppm: 1.88(3 H, singlet), 3.35(3H, singlet), 3.2–3.5(2H), 3.80(3H, singlet), 4.6–4.9 (2H + 1H), 6.7–6.9(1H + 1H), 7.1–7.5(10H), Mass spectrum (m/c): 596, 594, 592

2. To a solution of benhydryl 7β-(2',2'-dichloro-1'-methoxyethylideneimino)-7α-methoxy-3-acetoxymethyl-3-cephem-4-carboxylate(100 mg) in anhydrous chloroform(5 ml) were added quinoline(0.1 ml) and trimethylchlorosilane (0.5 ml). The mixture was stirred at room temperature for 5 hours, followed by addition of water. The mixture was extracted with chloroform, washed with water, dried and evaporated to dryness under reduced pressure to give 60 mg of the desire product.

EXAMPLE 23

Methyl 7β-chloroacetamido-7α-methoxy-3-methyl-3-cephem-4-carboxylate

1. Phosphorus pentachloride(360 mg) was dissolved in chloroform(24 ml). To this solution were added quinoline(0.24 ml) and methyl 7β-dichloroacetamido-3-methyl-3-cephem-4-carboxylate(340 mg) at room temperature. The reaction mixture was stirred at room temperature for 1 hour and then the solution was evaporated under reduced pressure. To the residue was added anhydrous tetrahydrofuran(40 ml) and precipitates were filtered off. The resulting solution contained methyl 7β-(1',2',2'-trichloroethylidenimino)-3-methyl-3-cephem-4-carboxylate, which can be used in the next reaction without purification. Isolation of this compound was carried out as follows: the tetrahydrofuran solution obtained above was poured into 10 % solution of dipotassium hydrogenphosphate and extracted with ethyl acetate. The extracts were washed with water, dried($Na_2SO_4$) and evaporated under reduced pressure at 20°C. to give 320 mg of methyl 7β-(1',2',2'-trichloroethylidenimino)-3-methyl-3-cephem-4-carboxylate as an oil. NMR($CDCl_3$) δ ppm: 2.17(3H, singlet), 3.27 and 3.50(2H, AB-quartet, J=19 Hz), 3.83(3H, singlet), 5.10 (1H, doublet, J=5 Hz), 5.55(1H, doublet, J=5 Hz), 6.42 (1H, singlet).

2. The product obtained above was dissolved in tetrahydrofuran(30 ml). After cooling to −70°C, the solution was stirred at −70°C. for 20 minutes with a methanol solution of lithium methoxide prepared from lithium(15 mg) and methanol(1 ml). To the reaction mixture was added acetic acid(0.1 ml). The solution was poured into water and extracted with ethyl acetate. The extracts were washed with water, dried($Na_2SO_4$) and evaporated under reduced pressure. The residue was purified by silica gel chromatography to afford 80 mg of methyl 7β-chloroacetamido-7α-methoxy-3-methyl-3-cephem-4-carboxylate, m.p. 123°–125°. IR $\nu_{max}^{Nujol}$ cm$^{-1}$; 3380, 1790, 1730, 1680. NMR($CDCl_3$) δ ppm: 2.25(3H, singlet), 3.20(2H, singlet), 3.53(3H, singlet), 3.73(3H, singlet), 4.07(2H, singlet), 4.98(1H, singlet), 7.43(1H, singlet).

EXAMPLE 24

2-(7β-Chloroacetamido-7α-methoxy-3-methyl-3-cephem-4-carbonyl)-triazolo[4,3-a]pyrido-3-one A methanol solution of lithium methoxide prepared from lithium(11 mg) and methanol(1 ml) was added at −78°C. to a solution of 2-[7-(1',2',2'-trichloroethylidenimino)-3-methyl-3-cephem-4-carbonyl[triazdo[4,3-a]pyrido-3-one in tetrahydrofuran(25 ml), which was prepared from 2-(7-dichloroacetamido-3-methyl-3-cephem-4-carbonyl)-triazolo[4,3-]pyrido-3-one(221 mg), phosphorus pentachloride (120 mg), quinoline(0.8 ml) and chloroform(10 ml) according to the same procedure as in Example 23 - (1). The reaction mixture was stirred at −78°C. for 10 minutes and treated with acetic acid(0.1 ml). The solution was poured into saturated sodium chloride solution and extracted with ethyl acetate. The extracts were washed with water, dried($Na_2SO_4$) and evaporated reduced pressure. The residue was chromatographed on silica gel to give 50 mg of 2-(7β-chloroacetamido-7α-methoxy-3-methyl-3-cephem-4-carbonyl)-triazolo[4,3-a]pyrido-3-one. NMR ($CD_3COCD_3$) δ ppm: 2.00(3H, singlet), 3.25 and 3.53(2H, AB-quartet, J=19 Hz), 3.42(3H, singlet), 3.77(2H, singlet), 5.20(1H, singlet), 6.4–6.7(1H, multiplet), 7.0–7.4(2H, multiplet), 7.6–7.8(1H, multiplet).

EXAMPLE 25

7β-Phenylacetamido-7α-methoxy-3-methyl-3-cephem-4-carboxylic acid

1. Benzhydryl 7β-(2'-bromo-1'-chloro-2'-phenylethylidenimino)-3-methyl-3-cephem-4-carboxylate in tetrahydrofuran was prepared from benzhydryl 7β-(2'-bromo-2'-phenylacetamido)-3-methyl-3-cephem-4-carboxylate(1.7 g), phosphorus pentachloride(0.81 g) and quinoline(0.6 ml) according to the same procedure as in Example 23 - (1). To this solution was added a solution of lithium(160 mg) in methanol (15 ml) at −70°C. The solution was stirred at −70°C. for 30 minutes, quenched with acetic acid(1.4 ml), poured into water and extracted with ethyl acetate. The extracts were washed with water and dried over sodium sulfate. The solvent was evaporated under reduced pressure and the residue was purified by silica gel chromatography to afford 0.9 g of benzhydryl 7β-phenylketenimino-7α-methoxy-3-methyl-3-cephem-4-carboxylate. IR $\nu_{max}^{Nujol}$ cm$^{-1}$: 2000, 1780, 1730. NMR($CDCl_3$) δ ppm: 2.20(3 H, singlet), 2.93 and 3.13(2H, AB-quartet), 3.70(3H, singlet), 5.00 (1H, singlet), 5.22(1H, singlet), 6.87(1H, singlet), 7.0–7.6(15H, multiplet).

1'. Following the same procedure as in Example 23 -(1) benzhydryl 7β(1',2'-dichloro- 2'-phenylethylidenimino)-3-methyl-3-cephem-4-carboxylate was obtained from benzhydryl 7β(2'-chloro-2'-phenylacetamido)-3-methyl- 3-cephem-4-carboxylate(1.06 g), phosphorus pentachloride (0.54 g) and quinoline(0.4 ml) and dissolved in tetrahydrofuran(40 ml). To this solution was added a methanol solution of lithium methoxide prepared from lithium(100 mg) and methanol(10 ml) at −70°C. The reaction mixture was stirred at −70°C. for 30 minutes, treated with acetic acid (1 ml), poured into water and extracted with ethyl acetate. The extracts were washed with water, dried ($Na_2SO_4$) and evaporated under reduced pressure. The residue was chromatographed on silica gel to give 0.7 g of benzhydryl 7β-phenylketenimino-7α-methoxy-3-methyl-3-cephem-4-carboxylate.

1''. Benzyhydryl 7β-(1',2'-dichloro-2'-phenylethylidenimino)-3-methyl-3-cephem-4-carboxylate was prepared from benzhydryl 7β-(2'-hydroxy-2'-phenylacetamido)-3-methyl-3-cephem-4-carboxylate(257 mg), phosphorus pentachloride(360 mg) and quinoline(0.26 ml) according to the same procedure as in Example 23 - (1) and treated in the same way as above to yield 120 mg of benzhydryl 7β-phenylketenimino-7α-methoxy-3-methyl-3-cephem-4-carboxylate.

2. Trifluoroacetic acid(0.2 ml) was added to a solution of benzhydryl 7β-phenylketenimino-7α-methoxy-3-methyl-3-cephem-4-carboxylate(50 mg) in chloroform(1 ml). The solution was stirred at room temperature for 1 hour and then evaporated under reduced pressure. The residue was dissolved in ethyl acetate and extracted with 10 % dipotassium hydrogen phosphate solution. The aqueous extracts were acidified with diluted hydrochloric acid to pH 2.2 and extracted with ethyl acetate. The extracts were washed with water, dried ($Na_2SO_4$) and evaporated under reduced pressure to give 27 mg of 7β-phenylacetamido-7α-methoxy-3-methyl-3-cephem-4-carboxylic acid: IR $\nu_{max}^{Nujol}$ cm$^{-1}$: 3250, 1770, 1700. NMR(CDCl$_3$) δ ppm. 2.20(3H, singlet), 3.17(2H, singlet), 3.38(3H, singlet), 3.63(2H, singlet), 4.95(1H, singlet), 6.92(1H, singlet), 7.22(5H, singlet).

EXAMPLE 26 p-Bromophenacyl 7β-phenylacetamido-7α-methoxy-3-acetoxymethyl- 3-cephem-4-carboxylate 1. p-Bromophenacyl 7β-(1',2'-dichloro-2'-phenylethylidenimino)-3-acetoxymethyl-3-cepham-4-carboxylate -carboxylate prepared from p-bromophenacyl 7β-(2'-chloro-2'-phenylacetamido)-3-acetoxymethyl-3-cephem-4-carboxylate (0.62 g), phosphorus pentachloride(0.3 g) and quinoline (0.2 ml) according to the same procedure as in Example 23 - (1) and dissolved in tetrahydrofuran 40 ml. To this solution was added a methanol solution of lithium methoxide prepared from lithium(40 mg) and methanol(3 ml) at −70°C. The reaction mixture was stirred at −70°C. for 30 minutes and treated with acetic acid(0.5 ml). The solution was poured into water and extracted with ethyl acetate. The extracts were washed with water, dried(Na$_2$SO$_4$) and evaporated under reduced pressure. The residue was purified by silica gel chromatography to afford 0.3 g of p-bromophenacyl 7β-phenylketenimino-7α-methoxy-3-acetoxymethyl-3-cephem-4-carboxylate. IR $\delta_{max}^{liquid}$ cm$^{-1}$: 2000, 1780, 1740, 1700. NMR(CDCl$_3$) δ ppm: 2.00(3H, singlet), 3.22 and 3.40(2H, AB-quartet, J=15 Hz), 3.60(3H, singlet), 4.97(1H, singlet), 4.90 and 5.18(2H, AB-quartet, J=16 Hz), 5.18(1H, singlet), 5.40(2H, singlet), 7.0–7.4(5H), 7.4–7.9 (4H).

2. To p-bromophenacyl 7β-phenylketenimino-7α-methoxy-3-acetoxymethyl-3-cephem-4-carboxylate(500 mg) in chloroform(10 ml) was added trifluoroacetic acid(2 ml). The solution was stirred at room temperature for 2 hours and then evaporated under reduced pressure to dryness. The residue was dissolved in ethyl acetate and washed with 10 % dipotassium hydrogen phosphate solution and water, dried over sodium sulfate and evaporated to give 470 mg of p-bromophenacyl 7β-phenylacetamido-7α-methoxy-3-acetoxymethyl-3-cephem-4-carboxylate. NMR(CDCl$_3$) δ ppm: 2.07(3H, singlet), 3.35 and 3.55(2H, AB-quartet, J=17 Hz), 3.40(3H, singlet), 3.67(2H, singlet), 5.03(2H, AB-quartet, J=13 Hz), 5.07(1H, singlet), 5.40(2H, singlet), 7.32(5H), 7.5–7.9(4H).

The same compound was also obtained in the following manner: a solution of p-bromophenacyl 7β-phenylketenimino-7α-methoxy-3-acetoxymethyl-3-cephem-4-carboxylate(100 mg) in tetrahydrofuran was adjusted to pH 3.0 with diluted hydrochloric acid. The reaction mixture was stirred at 10°C. overnight. The solution was poured into water and extracted with ethyl acetate. The extracts were washed with water, dried over sodium sulfate and evaporated under reduced pressure. The residue was chromatographed on silica gel to give 20 mg of p-bromophenacyl 7β-phenylacetamido-7αmethoxy-3-acetoxymethyl-3-cephem-4-carboxylate.

EXAMPLE 27

Benzhydryl 7β-propionamido-7α-methoxy-3-methyl-3-cephem-4-carboxylate

1. Benzhydryl7β-(2'-bromo-1'-chloropropylidenimino)-3-methyl-3-cephem-4-carboxylate was prepared from benzhydryl 7β-(2'-bromopropionamido)-3-methyl-3-cephem-4-carboxylate(515 mg), phosphorus pentachloride(270 mg) and quinoline(0.2 ml) according to the same procedure as in Example 23 - (1) and dissolved in tetrahydofuran (40 ml). To this solution was added a methanol solution of lithium methoxide prepared from lithium(50 mg) and methanol(4 ml) at −70°C. and the reaction mixture was stirred at −70°C. for 30 minutes. After adding acetic acid(0.4 ml) the solution was poured into water and extracted with ethyl acetate. The extracts were washed with water, dried (Na$_2$SO$_4$) and evaporated under reduced pressure to give 480 mg of a crude product of benzhydryl 7β-methylketenimino-7α-methoxy-3-methyl-3-cephem-4-carboxylate. IR $\nu_{max}^{liquid}$ cm$^{-1}$: 2020, 1770, 1710.

2. Benzhydryl 7β-methylketenimino-7α-methoxy-3-methyl-3-cephem-4-carboxylate obtained above was dissolved in chloroform(20 ml), to which was added trifluoroacetic acid(1 ml). The solution was stirred at room temperature for 2 hours, and then evaporated under reduced pressure. The residue was dissolved in ethyl acetate, which was washed with water and dried over sodium sulfate. To this ethyl acetate solution was added excess diphenyldiazomethane and the mixture was kept at room temperature overnight. The solution was evaporated under reduced pressure and the residue was washed with n-hexane and chromatographed on silica gel to give 90 mg of pure benzhydryl 7β-propionamido-7α-methoxy-3-methyl-3-cephem-4-carboxylate as oils. IR $\nu_{max}^{liquid}$ cm$^{-1}$: 3350, 1780, 1725, 1690. NMR(CDCl$_3$) δ ppm: 1.15(3H, triplet, J=6 Hz), 2.10 (3H, singlet), 2.30(2H, quartet, J=6 Hz), 3.13(2H, singlet), 3.43(3H, singlet), 4.97(1H, singlet), 6.65(1H, broad singlet), 6.82(1H, singlet), 7.1–7.6(10H, multiplet).

EXAMPLE 28

Methyl 7β-acetamido-7αmethoxy-3-methyl-3-cephem-4-carboxylate

Methyl 7β-(2'-bromo-1'-chloroethylidenimino)-3-methyl-3-cephem-4-carboxylate was prepared from methyl 7β-bromoacetamido-3-methyl-3-cephem-4-carboxylate(1.34 g), phosphorus pentachloride(1.5 g) and quinoline(1 ml) according to the same procedure as in Example 23 - (1) and dissolved in tetrahydrofuran(80 ml). To this solution was added a methanol solution of lithium methoxide prepared from lithium(200 mg) and methanol(20 ml) at −70°C. The reaction mixture was stirred at −70°C. for 30 minutes, then trifluoroacetic acid(2.5 ml) was added and stirring was continued at room temperature for 10 minutes. The mixture was poured into water and extracted with ethyl acetate. The extracts were washed with 10 % dipotassium hydrogen phosphate solution and water, dried over sodium sulfate and evaporated under reduced pressure. The residue was chromatographed on silica gel to afford 250 mg of methyl 7β-acetamido-7α-methoxy-3-methyl-3-cephem-4-carboxylate. IR $\nu_{max}^{liquid}$ cm $^{-1}$: 3220, 1770, 1730, 1690. NMR(CDCl₃) δ ppm: 2.13(6H, singlet), 3.20 and 3.37(2H, AB-quartet, J=17 Hz), 3.55(3H, singlet), 3.83(3H, singlet), 5.07(1H, singlet), 7.52(1H, singlet).

EXAMPLE 29

7β-(α-Thienylacetamido)-7α-methoxy-3-acetoxymethyl-3cephem-4-carboxylic acid

Benzhydryl 7η-(1',2'-dichloro-2'-α-thienylethylidenimino)-3-acetoxymethyl-3-cephem-4-carboxylate was prepared from benzhydryl 7β-(α-thienylchloroacetamido)-3-acetoxymethyl-3-cephem-4-carboxylate(597 mg), phosphorus pentachloride(360 mg) and quinoline(0.24 ml) according to the same procedure as in Example 23 - (1). To this solution was added a methanol solution of lithium methoxide prepared from lithium(12 mg) and methanol(2ml) at −70°C. and the reaction mixture was stirred at −70°C. for 40 minutes. To the resulting solution was added trifluoroacetic acid(5 ml) and stirring was continued at room temperature for 40 minutes. The solution was evaporated under reduced pressure to dryness and the residue was dissolved in ethyl acetate, which was extracted with a pH 7.5 buffer(disodium hydrogen phosphatepotassium dihydrogen phosphate). The aqueous extracts were adjusted to pH 2.0 with diluted hydrochloric acid and extracted with ethyl acetate. The combined extracts were washed with water, dried (MgSO₄) and evaporated to give 85 mg of 7β-(α-thienylacetamido)-7α-methoxy-3-acetoxymethyl-3-cephem-4-carboxylic acid. NMR(CD₃SOCD₃ + D₂O) δ ppm: 2.01(3H, singlet), 3.20(1H, doublet, J=18 Hz), 3.33(1H, doublet, J=18 Hz), 3.40(3H, singlet), 3.85(2H, singlet), 4.88(2H, almost singlet), 5.04(1H, singlet), 6.90–7.45(3H, multiplet).

EXAMPLE 30

7β-(α-Thienylacetamido)-7α-methoxy-3-carbamoyloxymethyl-3-cephem-4-carboxylic acid Benzhydryl 7-(1',2'-dichloro-2'-α-thienylethylidenimino)-3-carbamoyloxymethyl-3-cephem-4-carboxylate was prepared from benzhydryl 7β-)α-thienylchloroacetamido)-3-carbamoyloxymethyl-3-cephem-4-carboxylate(597 mg), phosphorus pentachloride(220 mg) and quinoline(0.15 ml) according to the same procedure as in Example 23 - (1) and dissolved in tetrahydrofuran(40 ml). To the solution was added a methanol solution of lithium methoxide prepared from lithium(12 mg) and methanol(4 ml) at −70°C. The reaction mixture was stirred at −70°C. for 30 minutes. After the addition of trifluoroacetic acid (5 ml) the solution was stirred at room temperature for 40 minutes. The solution was evaporated under reduced pressure to dryness and the residue was extracted with ethyl acetate, which was re-extracted with a pH 7.5 buffer (disodium hydrogen phosphate-potassium dihydrogen phosphate). The aqueous extracts were acidified to pH 2.0 with diluted hydrochloric acid and extracted with ethyl acetate. The combined extracts were washed with water, dried over magnesium sulfate and evaporated to give 60 mg of 7β-)α-thienylacetamido)-7α-methoxy-3-carbamoyloxymethyl-3-cephem-4-carboxylic acid. IR ν$_{max}^{Nujol}$ cm⁻¹: 3420, 3330, 3230, 1783, 1715, 1680, 1665. NMR(CD₃CN) δ ppm: 3.53(3H, singlet), 3.38(1H, doublet, J=18 Hz), 3.60(1H, doublet, J=18 Hz), 3.90(2H, singlet), 4.88(2H, singlet), 5.07(1H, singlet), 6.95–7.40(3H, multiplet).

EXAMPLE 31

Methyl 6β-phenylacetamido-6αmethoxy-2,2-dimethylpenam-3-carboxylate

1. Methyl 6-(1',2'-dichloro-2'-phenylethylidenimino)-2,2-dimethylpenam-3-carboxylate was prepared from methyl 6-(2'-chloro-2'-phenylacetamido)-2,2-dimethylpenam-3-carboxylate(300 mg), phosphorus pentachloride (300 mg) and quinoline (0.2 ml) according to the same procedure as in Example 23 - (1) and dissolved in tetrahydrofuran (30 ml). To this solution was added a methanol solution of lithium methoxide prepared from lithium(40 mg) in methanol(3 ml) at −70°C. The reaction mixture was stirred at −70°C. for 30 minutes and treated with acetic acid(0.5 ml). The solution was poured into water and extracted with ethyl acetate. The extracts were washed with water, dried(Na₂SO₄) and evaporated under reduced pressure. The residue was purified by silica gel chromatography to give 180 mg of methyl 6β-phenylketenimino-6α-methoxy-2,2-dimethylpenam-3-carboxylate mp. 80°C. IR ν$_{max}^{Nujol}$ cm⁻¹: 2000, 1765, 1740. NMR(CDCl₃) δ ppm: 1.43 (3H, singlet), 1.47(3H, singlet), 3.65(3 H, singlet), 3.75 (3H, singlet), 4.38(1H, singlet), 5.17(1H, singlet), 5.50 (1H, singlet), 7.2–7.6(5H, multiplet).

2. A solution of methyl 6β-phenylketenimino-6α-methoxy-2,2-dimethylpenam-3-carboxylate(100 mg) in tetrahydrofuran was adjusted to pH 4.0 with diluted hydrochloric acid. The reaction mixture was stirred at room temperature overnight. The solution was poured into water and extracted with ethyl acetate. The extracts were washed with water, dried(Na₂SO₄) and evaporated under reduced pressure. The residue was chromatographed on silica gel to afford 20 mg of methyl 6β-phenylacetamido-6α-methoxy-2,2-dimethylpenam-3-carboxylate. IR ν$_{max}^{Nujol}$ cm⁻¹3330, 1780, 1750, 1695, 1670. NMR(CDCl₃) δ ppm: 1.35(6H, singlet), 3.36(3H, singlet), 3.61 (2H, singlet), 3.72(3H, singlet), 4.34(1H, singlet), 5.52(1H, singlet), 7.25(5H, singlet).

EXAMPLE 32

Methyl 7β-diphenylacetamido-7α-methoxy-3-methyl-3-cepham-4-carboxylate

1. In anhydrous chloroform(32 ml) was dissolved phosphorus pentachloride(720 mg), to which was added quinoline(0.52 ml). To the mixture was added under icecooling methyl 7-(2',2'-diphenyl-2'-hydroxyacetamido)-3-methyl-3-cephem-4-carboxylate(480 mg). The reaction mixture was stirred under ice-cooling for 40 minutes and the solvent was distilled off under reduced pressure. To the residue was added anhydrous tetrahydrofuran(40 ml) and crystalline substances were filtered off. After cooling to −78°C the filtrate was stirred at −70°-−78°C. for 20 minutes with a methanol solution of lithium methoxide prepared from lithium(48 mg) and methanol(6ml), followed by addition of acetic acid(0.5 ml). The reaction mixture was poured into water, extracted with ethyl acetate, which was washed with water, dried and evaporated to dryness. The residue was purified by silica gel chromatography to give 65 mg of methyl 7β-diphenylketeneimino-7α-methoxy-3-methyl-3cephem-4-carboxylate. IR $\nu_{max}^{liquid\ film}$ cm$^{-1}$ : 1997, 1775, 1730. NMR(CDCl$_3$) δ ppm: 2.16(3H, singlet), 2.80(2H, singlet), 3.56(3H, singlet), 3.82(3H, singlet), 4.92(1H, singlet), 7.2–7.5(10H).

2. Methyl 7β-diphenylketeneimino-7α-methoxy-3-methyl-3-cephem-4-carboxylate(85 mg) was dissolved in chloroform(3 ml), to which was added trifluoroacetic acid (0.3 ml). The mixture was stirred at room temperature for 30 minutes and the solvent was distilled off under reduced pressure. To the residue was added water. The mixture was extracted with ethyl acetate, washed with water and dried to give 83 mg of the desired product. IR $\nu_{max}^{Nujol}$ cm$^{-1}$: 3350, 1785, 1730, 1690.

What is claimed is:
1. A process for the preparation of a compound having the formula

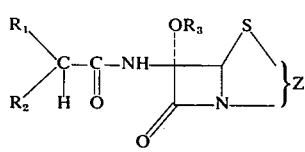

(I)

wherein R$_1$ is a hydrogen atom, a halogen atom, an alkyl group having from 1 to 4 carbon atoms, or an aryl group; R$_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; R$_3$ is an alkyl group having from 1 to 4 carbon atoms;

Z is a fragment of the formula

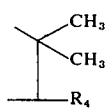

or

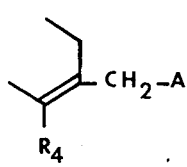

where R$_4$ is a carboxyl group or a conventional protected carboxyl group;
A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;
which comprises reacting an acylamino compound having the formula

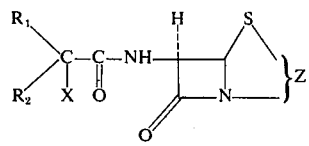

(II)

wherein R$_1$, R$_2$ and Z are the same as above and X is a hydroxy group or a halogen atom with a halogenating agent to give a halogenoimine having the formula

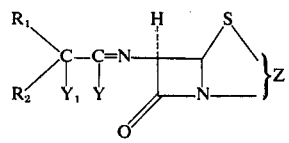

(III)

wherein R$_1$, R$_2$ and Z are the same as above and Y$_1$ and Y may be the same or different and each is a halogen atom, reacting the latter compound (III) with an equimolar amount of an alkali metal alkoxide having the formula

R$_3$OM   (IV)

wherein R$_3$ is the same as above and M is an alkali metal in the presence of one equivalent amount of a base to give an alkoxyketeneimine having the formula

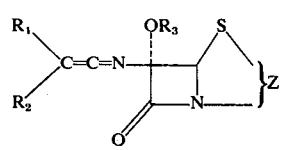

(V)

wherein R$_1$, R$_2$, R$_3$ and Z are the same as above and subjecting the later compound (V) to hydration.

2. The process of claim 1 in which the acylamino compound (II) is reacted with the halogenating agent in the presence of a tertiary amine.

3. The process of claim 2 in which the tertiary amine is quinoline, pyridine, diethylaniline or dimethylaniline.

4. A process for the preparation of a compound having the formula

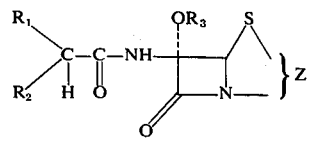

(I)

wherein R$_1$ is a hydrogen atom, a halogen atom, an alkyl group having from 1 to 4 carbon atoms, or an aryl group; R$_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; R$_3$ is an alkyl group having from 1 to 4 carbon atoms;

Z is a fragment of the formula

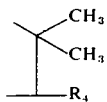

or

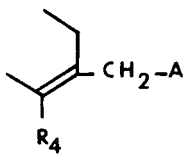

wherein R₄ is a carboxyl group or a conventional protected carboxyl group;

A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;

which comprises reacting an acylamino compound having the formula

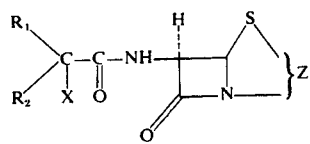

wherein $R_1$, $R_2$ and Z are the same as above and X is a hydroxy group or a halogen atom with a halogenating agent to give a halogenoimine having the formula

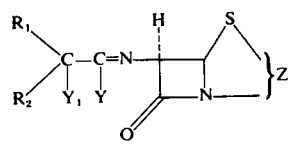

wherein $R_1$, $R_2$ and Z are the same as above and $Y_1$ and Y may be the same or different and each is a halogen atom reacting the latter compound (III) with two equimolar amounts of an alkali metal alkoxide having the formula

     (IV)

wherein $R_3$ is the same as above and M is an alkali metal in the presence of one equivalent amount of a base to give a dialkoxyimino compound having the formula

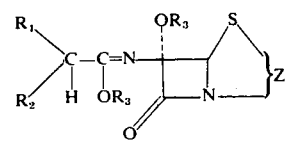

wherein $R_1$, $R_2$, $R_3$ and Z are the same as above, reacting the latter compound (VI) with a halogenosilyl compound or an acid and treating the resulting compound with water.

5. A process for the preparation of a compound having the formula

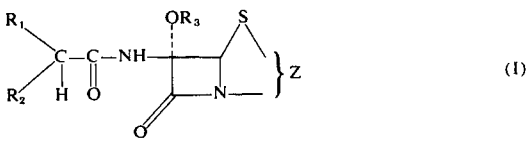

wherein $R_1$ is a hydrogen atom, a halogen atom, an alkyl group having from 1 to 4 carbon atoms, or an aryl group; $R_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; $R_3$ is an alkyl group having from 1 to 4 carbon atoms;

Z is a fragment of the formula

or

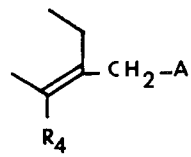

wherein $R_4$ is a carboxyl group or a conventional protected carboxyl group;

A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;

which comprises reacting a halogenoimine having the formula

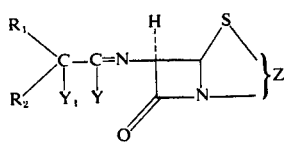

wherein $R_1$, $R_2$ and Z are the same as above and $Y_1$ and Y may be the same or different and each is a halogen atom with an equimolar amount of an alkali metal alkoxide having the formula

     (IV)

wherein $R_3$ is the same as above and M is an alkali metal in the presence of one equivalent amount of a base to give an alkoxyketeneimine having the formula

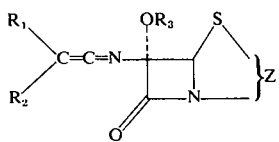

(V)

wherein $R_1$, $R_2$, $R_3$ and Z are the same as above and subjecting the latter compound (V) to hydration.

6. The process of claim 5 in which the base is a tertiary amine.
7. The process of claim 6 in which the tertiary amine is quinoline, pyridine, diethylaniline, dimethylaniline, triethylamine or diazabicyclooctane.
8. The process of claim 5 in which the base is the alkali metal alkoxide having the formula (IV).
9. The process of claim 8 in which the alkali metal alkoxide having the formula (IV) is lithium methoxide.
10. A process for the preparation of a compound having the formula

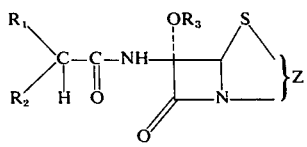

(I)

wherein $R_1$ is a hydrogen atom, a halogen atom, an alkyl group having from 1 to 4 carbon atoms, or an aryl group;
$R_2$ is a hydrogen atom, a halogen atom, an alkyl group having from 1 to 4 carbon atoms, an aryl group, an alkylthio group having from 2 to 4 carbon atoms, an arlythio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; $R_3$ is an alkyl group having from 1 to 4 carbon atoms; Z is a fragment of the formula

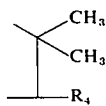

or

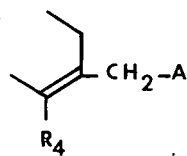

wherein $R_4$ is a carboxyl group or a conventional protected carboxyl group;
A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;
which comprises reacting a halogenoimine having the formula

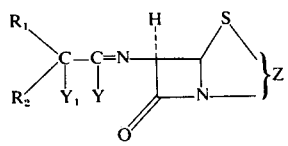

(III)

wherein $R_1$, $R_2$ and Z are the same as above and $Y_1$ and Y may be the same or different and each is a halogen atom with two equimolar amounts of an alkali metal alkoxide having the formula $R_3OM$ (IV)

wherein $R_3$ is the same as above and M is an alkali metal in the presence of one equivalent amount of a base to give a dialkoxyimino compound having the formula

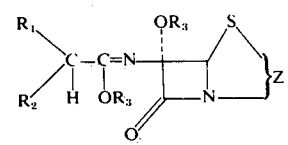

(VI)

wherein $R_1$, $R_2$, $R_3$ and Z are the same as above, reacting the latter compound (VI) with a halogenosilyl compound or an acid and treating the resulting compound with water.

11. The process of claim 10 in which the base is a tertiary amine.
12. The process of claim 11 in which the tertiary amine is quinoline, pryidine, diethylaniline, dimethylaniline, triethylamine or diazabicyclooctane.
13. The process of claim 10 in which the base is the alkali metal alkoxide having the formula (IV).
14. The process of claim 13 in which the alkali metal alkoxide having the formula (IV) is lithium methoxide.
15. A process for the preparation of a compound having the formula

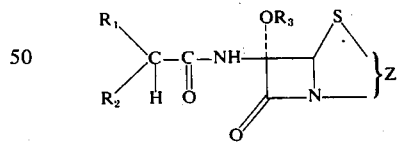

(I)

wherein $R_1$ is a hydrogen atom, a halogen atom, an alkyl group having from 1 to 4 carbon atoms, or an aryl group; $R_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group, a 5- or 6-membered heterocyclic thio group; $R_3$ is an alkyl group having from 1 to 4 carbon atoms;
Z is a fragment of the formula

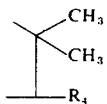

or

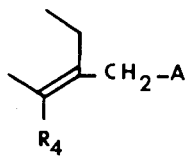

wherein R₄ is a carboxyl group or a conventional protected carboxyl group;
A is a hydrogen atom, an azido grouup or the formula -B-E in which B is oxygen or sulfur and E is an acyl group, an alkyl group having from 1 to 4 carbon atoms, optionally substituted-carbamoyl, -thiocarbamoyl or -heterocyclic group;
which comprises subjecting an alkoxyketeneimine having the formula

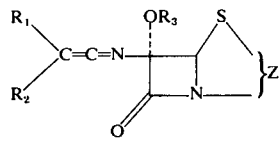 (V)

wherein $R_1$, $R_2$, $R_3$ and Z are the same as above to hydration.

16. The process of claim 15 in which the hydration is carried out by usng an aqueous mineral acid.

17. The process of claim 16 in which the aqueous mineral acid is aqueous hydrochloric acid, aqueous hydrobromic acid, aqueous sulfuric acid or aqueous phosphoric acid.

18. The process of claim 15 in which the hydration is carried out by using an organic acid.

19. The process of claim 18 in which the organic acid is acetic acid, trichloroacetic acid, tribromoacetic acid or trifluoroacetic acid.

20. A process for the preparation of a compound having the formula

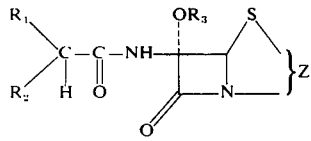 (I)

wherein $R_1$ is a hydrogen atom, a halogen atom, an alkyl group having from 1 to 4 carbon atoms, or an aryl group; $R_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; $R_3$ is an alkyl group having from 1 to 4 carbon atoms;
Z is a fragment of the formula

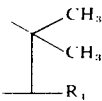

or

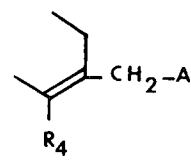

wherein R₄ is a carboxyl group or a conventional protected carboxyl group;
A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;
which comprises subjecting a dialkoxyimino compound having the formula

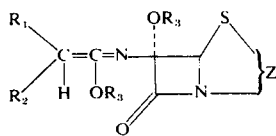 (VI)

wherein $R_1$, $R_2$, $R_3$ and Z are the same as above with a halogenosilyl compound or an acid and treating the resulting compound with water.

21. The process of claim 20 in which the halogenosilyl compound is a dialkyldihalogenosilane or a trialkylhalogenosilane.

22. The process of claim 21 in which the dialkyldihalogenosilane is dimethyldichlorosilane, diethyldichlorosilane, dimethyldibromosilane or diethyldibromosilane.

23. The process of claim 21 in which the trialkylhalogenosilane is trimethylchlorosilane, triethylchlorosilane, trimethylbromosilane or triethylbromosilane.

24. A process for the preparation of a compound having the formula

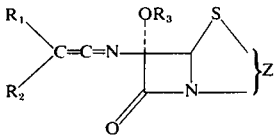 (V)

wherein $R_1$ is a hydrogen atom, a halogen atom, an alkyl group having from 1 to 4 carbon atoms, or an aryl group; $R_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; $R_3$ is an alkyl group having from 1 to 4 carbon atoms;

Z is a fragment of the formula

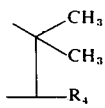

or

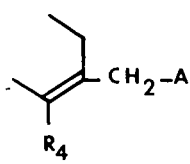

wherein $R_4$ is a carboxyl group or a conventional protected carboxyl group;

A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;

which comprises reacting a halogenoimine having the formula

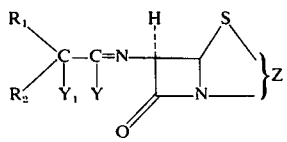 (III)

wherein $R_1$, $R_2$ and Z are the same as above and $Y_1$ and Y may be the same or different and each is a halogen atom, reacting the latter compound (III) with an equimolar amount of an alkali metal alkoxide having the formula $R_3OM$  (IV)

wherein $R_3$ is the same as above and M is an alkali metal in the presence of one equivalent amount of a base.

25. A process for the preparaton of a compound having the formula

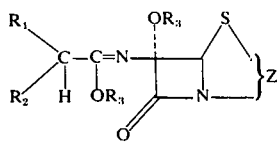 (VI)

wherein $R_1$ is a hydrogen atom, a halogen atom, an alkyl group having from 1 to 4 carbon atoms, or an aryl group; $R_2$ is a hydrogen atom, a halogen atom, an alkyl group having from 1 to 4 carbon atoms, an aryl group, an alkylthio group having from 2 to 4 carbon atoms, an arylthio group, an azidoalkylthio group having from 1 to 4 carbon atoms, a cyanoalkylthio group having from 1 to 4 carbon atoms in the alkyl moiety, an alkylsulfonyl group having from 1 to 4 carbon atoms, a 5- or 6-membered heterocyclic group, a 5- or 6-membered heterocyclic oxy group or a 5- or 6-membered heterocyclic thio group; $R_3$ is a alkyl group having from 1 to 4 carbon atoms;

Z is a fragment of the formula

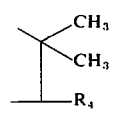

or

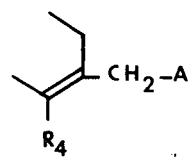

hwerin $R_4$ is a carboxyl group or a conventional protected carboxyl group;

A is a hydrogen atom, an azido group or the formula -B-E in which B is oxygen or sulfur and E is an acyl group, an alkyl group having from 1 to 4 carbon atoms, optionally substituted-carbamoyl, -thiocarbamoyl or -heterocyclic group;

which comprises reacting a halogenoimine having the formula

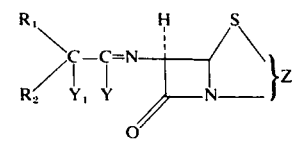 (III)

wherein $R_1$, $R_2$ and Z are the same as above and $Y_1$ and Y may be the same or different and each is a halogen atom with two equimolar amounts of an alkali metal alkoxide having the formula $R_3OM$  (IV)

wherein $R_3$ is the same as above and M is an alkali metal in the presence of one equivalent amount of a base.

26. The process of claim 4, in which the acylamino compound (II) is reacted with the halogenating agent in the presence of a tertiary amine.

27. The process of claim 26 in which the tertiary amine is quinoline, pyridine, diethylaniline or dimethylaniline.

* * * * *

UNITED STATES PATENT OFFICE
CERTIFICATE OF CORRECTION

PATENT NO. : 3,960,845
DATED : June 1, 1976
INVENTOR(S) : TETSUO HIRAOKA et al

It is certified that error appears in the above-identified patent and that said Letters Patent are hereby corrected as shown below:

1) Column 5, line 26: replace "solvent" with -- solvents --.

2) Column 6, line 58: replace "perchloric" with -- perchromic --.

3) Column 7, line 60: replace "thiozolin" with -- thiazolin --.

4) Column 9, in the Table, under "Tested compounds": in the third compound, replace the entire compound with:
--- 7β-(3-isoxazolyloxy)acetamido-7α-methoxy-3-(1-methyl-1H-tetrazol-5-yl)thiomethyl-3-cephem-4-carboxylic acid ---.

5) Column 14, line 26: before "-78°C.", replace "a" with -- at --.

6) Column 15, line 27: replace "as" with --- was ---.

7) Column 15, line 27: replace "a" with -- at --.

8) Column 15, line 37: replace "wate" with --- water ---.

9) Column 16, line 42: replace "1." with --- (1)' ---.

10) Column 17, line 12: after "methyl", delete ")".

UNITED STATES PATENT OFFICE
CERTIFICATE OF CORRECTION

PATENT NO. : 3,960,845
DATED : June 1, 1976
INVENTOR(S) : TETSUO HIRAOKA et al

It is certified that error appears in the above-identified patent and that said Letters Patent are hereby corrected as shown below:

11) Column 18, line 64: replace "mixture" (first occurrence) with --- added ---.

12) Column 19, line 9: replace "ere" with --- were ---.

13) Column 19, line 54: replace "5.55(52H" with --- 5.55(2H ---.

14) Column 21, line 24: replace "A$_2$B2" with --- A$_2$B$_2$ ---.

15) Column 23, line 5: replace "207(3singlet)" with --- 2.07(3H, singlet) ---.

16) Column 23, line 38: replace "recrystalliation" with --- recrystallization ---.

17) Column 23, last line: replace "5.06)" with -- 5.06( --.

18) Column 26, line 7: after "product.", delete "des".

19) Column 27, lines 53-54: replace "[triaz-do" with --- triazolo ---.

20) Column 31, line 9: replace "3cephem" with -- 3-cephem --.

21) Column 31, line 10: "7η" should be --- 7β ---.

UNITED STATES PATENT OFFICE
CERTIFICATE OF CORRECTION

PATENT NO. : 3,960,845
DATED : June 1, 1976
INVENTOR(S) : TETSUO HIRAOKA et al

It is certified that error appears in the above-identified patent and that said Letters Patent are hereby corrected as shown below:

22) Column 42, line 31, Claim 25: replace "hwerin" with --- wherein ---.

Signed and Sealed this

Eighth Day of February 1977

[SEAL]

Attest:

RUTH C. MASON
*Attesting Officer*

C. MARSHALL DANN
*Commissioner of Patents and Trademarks*